United States Patent
Carr et al.

(10) Patent No.: US 8,263,335 B2
(45) Date of Patent: *Sep. 11, 2012

(54) METHODS FOR HIGH FIDELITY PRODUCTION OF LONG NUCLEIC ACID MOLECULES WITH ERROR CONTROL

(75) Inventors: Peter A. Carr, Medford, MA (US); Brian Y. Chow, Cambridge, MA (US); Joseph M. Jacobson, Newton, MA (US); David W. Mosley, Cambridge, MA (US); Christopher Emig, Napa, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,807

(22) Filed: Apr. 25, 2011

(65) Prior Publication Data
US 2011/0201057 A1    Aug. 18, 2011

Related U.S. Application Data

(62) Division of application No. 10/733,855, filed on Dec. 10, 2003, now Pat. No. 7,932,025.

(60) Provisional application No. 60/432,556, filed on Dec. 10, 2002.

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |
| *C07H 21/00* | (2006.01) |

(52) U.S. Cl. ...... 435/6.1; 435/6.11; 435/6.12; 435/91.1; 435/91.2; 536/23.1; 536/24.3; 536/24.33; 536/25.3

(58) Field of Classification Search ............ 435/6, 91.1, 435/91.2, 91.51, 183, 283.1, 287.1, 287.2, 435/6.1, 6.11, 6.12; 436/94; 536/23.1, 24.3, 536/24.33, 25.3
See application file for complete search history.

(56) References Cited

U.S. PATENT DOCUMENTS

| | | | |
|---|---|---|---|
| 6,939,673 B2 * | 9/2005 | Bass et al. .................... 435/6.19 |
| 7,932,025 B2 * | 4/2011 | Carr et al. .................... 435/6.11 |
| 2003/0171325 A1 * | 9/2003 | Gascoyne et al. .............. 514/44 |

* cited by examiner

*Primary Examiner* — Frank W Lu
(74) *Attorney, Agent, or Firm* — Norma E. Henderson

(57) ABSTRACT

A method for synthesizing a nucleic acid having a desired sequence and length comprises providing a solid support having an immobilized nucleic acid, performing a nucleic acid addition reaction to elongate the immobilized nucleic acid by adding a nucleotide or an oligonucleotide to the nucleic acid, determining whether the nucleotide or the oligonucleotide is added to the nucleic acid by detecting whether there is an increase in electrophoretic force applied to the solid support when an electric field and a magnetic field gradient are applied to the support, wherein the increase in electrophoretic force applied to the support is caused by adding the nucleotide or the oligonucleotide to the nucleic acid, repeating the addition reaction and determination steps if the nucleotide or the oligonucleotide is not added to the nucleic acid, and continuing until the immobilized nucleic acid has a desired sequence and length.

3 Claims, 31 Drawing Sheets

STEP 1
STEP 2
STEP 3
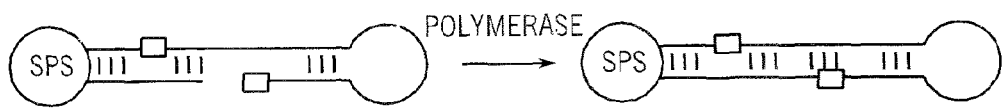
STEP 4
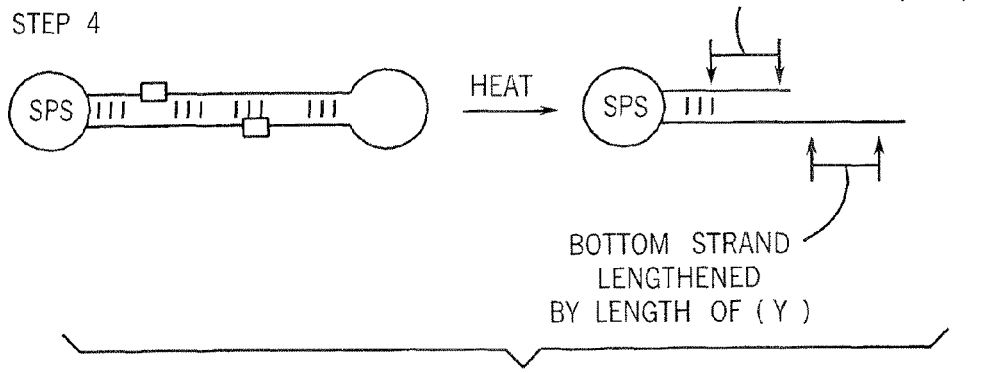
FIG. 8C

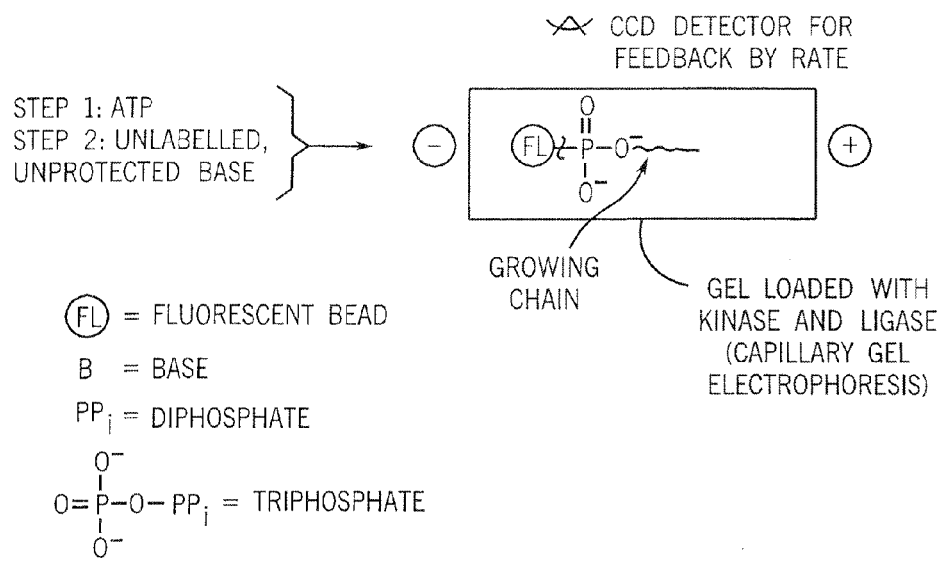
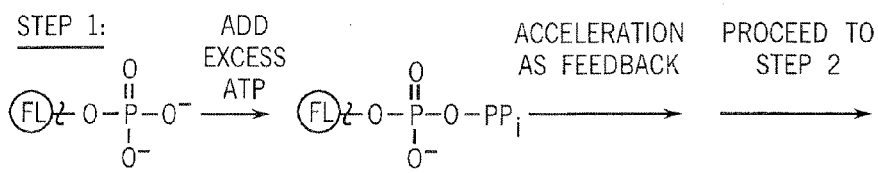
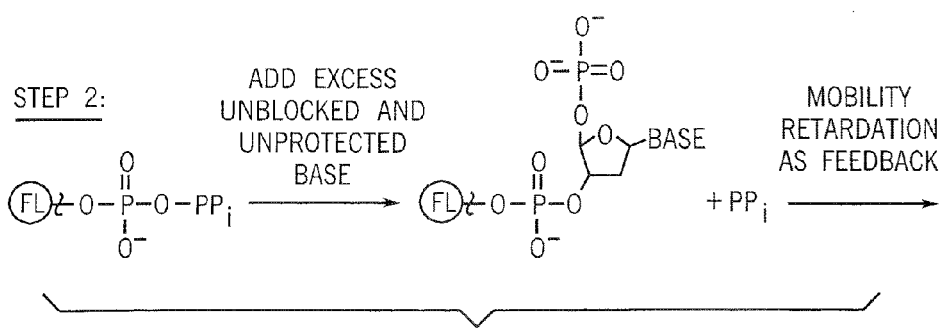
FIG. 10

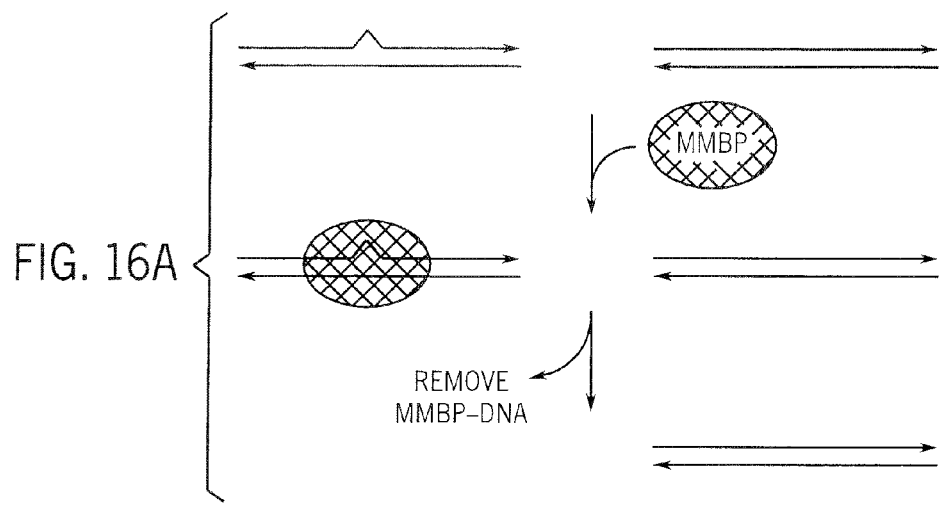
FIG. 16A
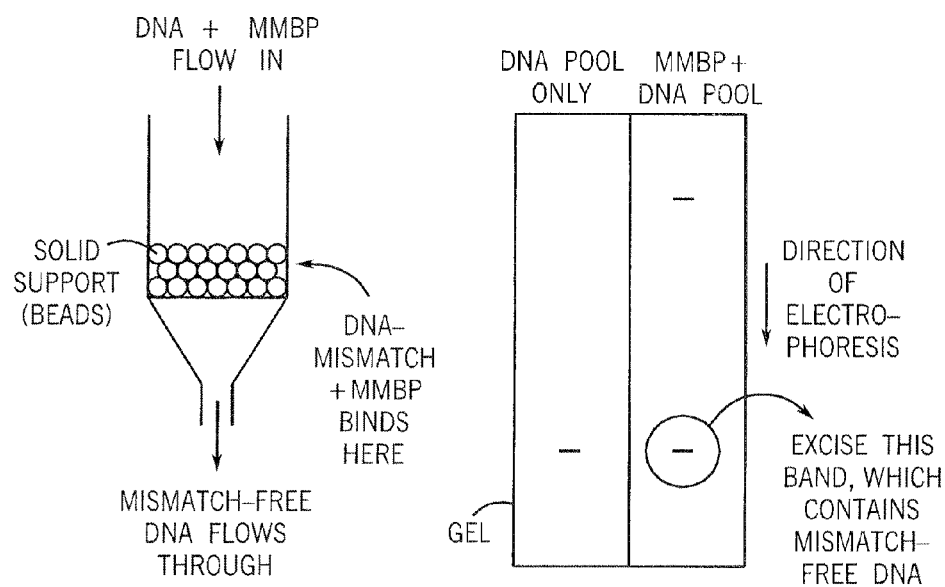
FIG. 16B
FIG. 16C

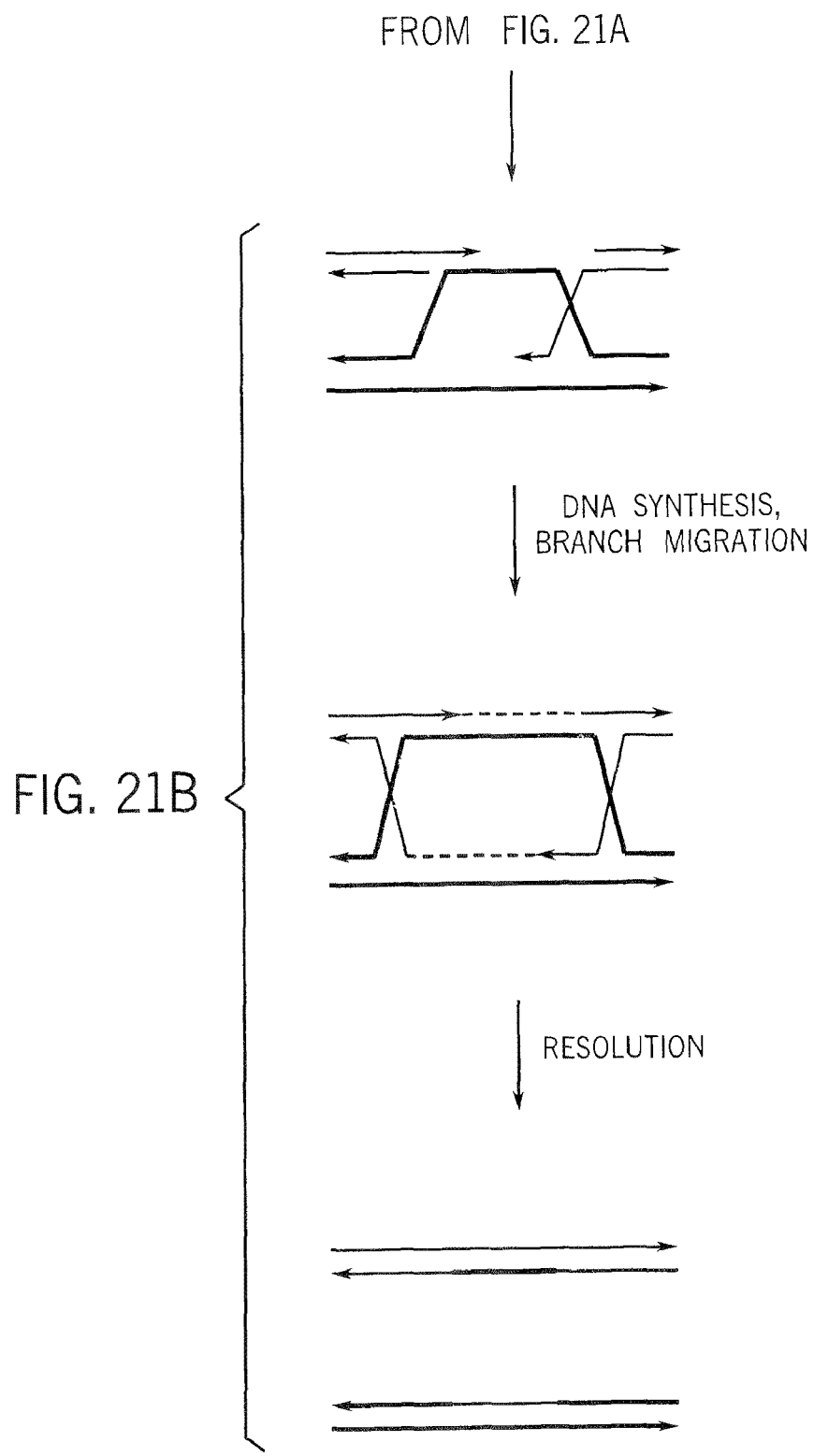

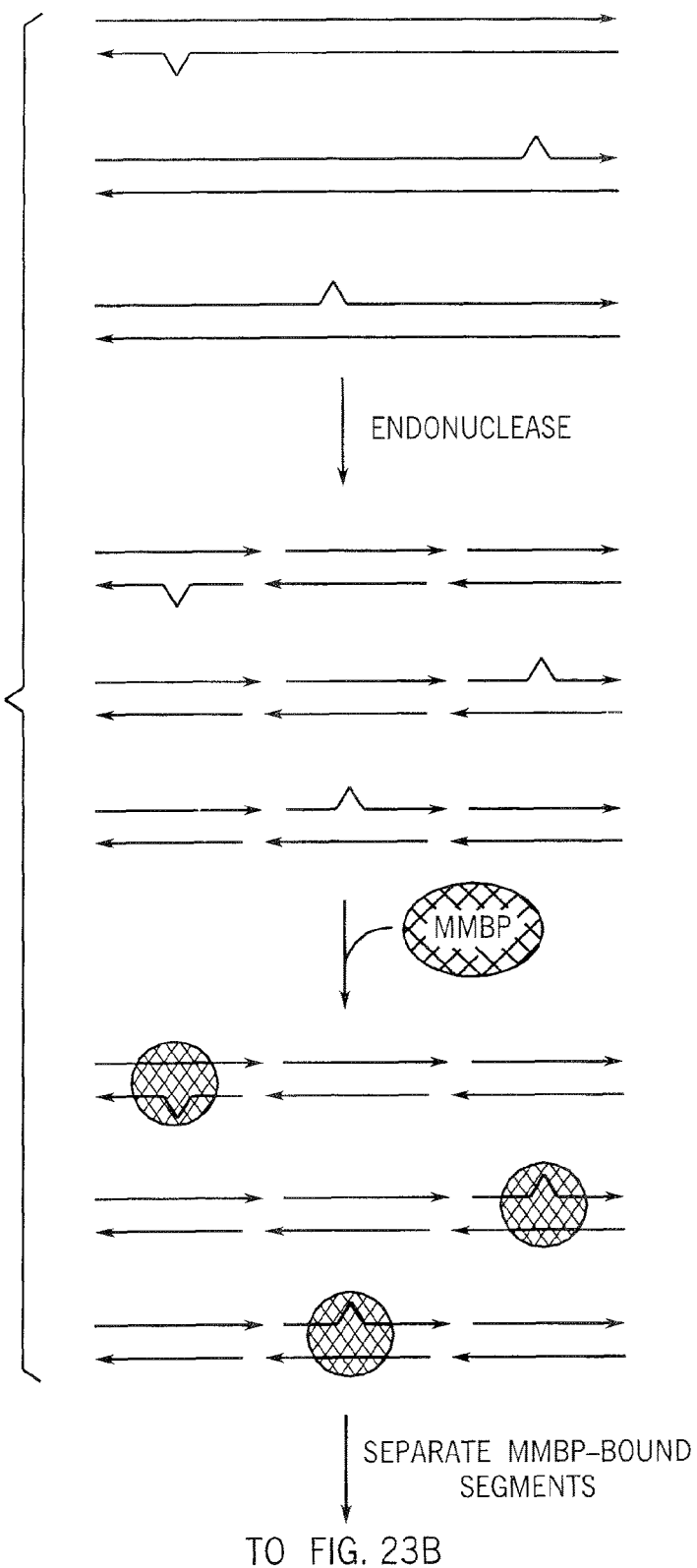

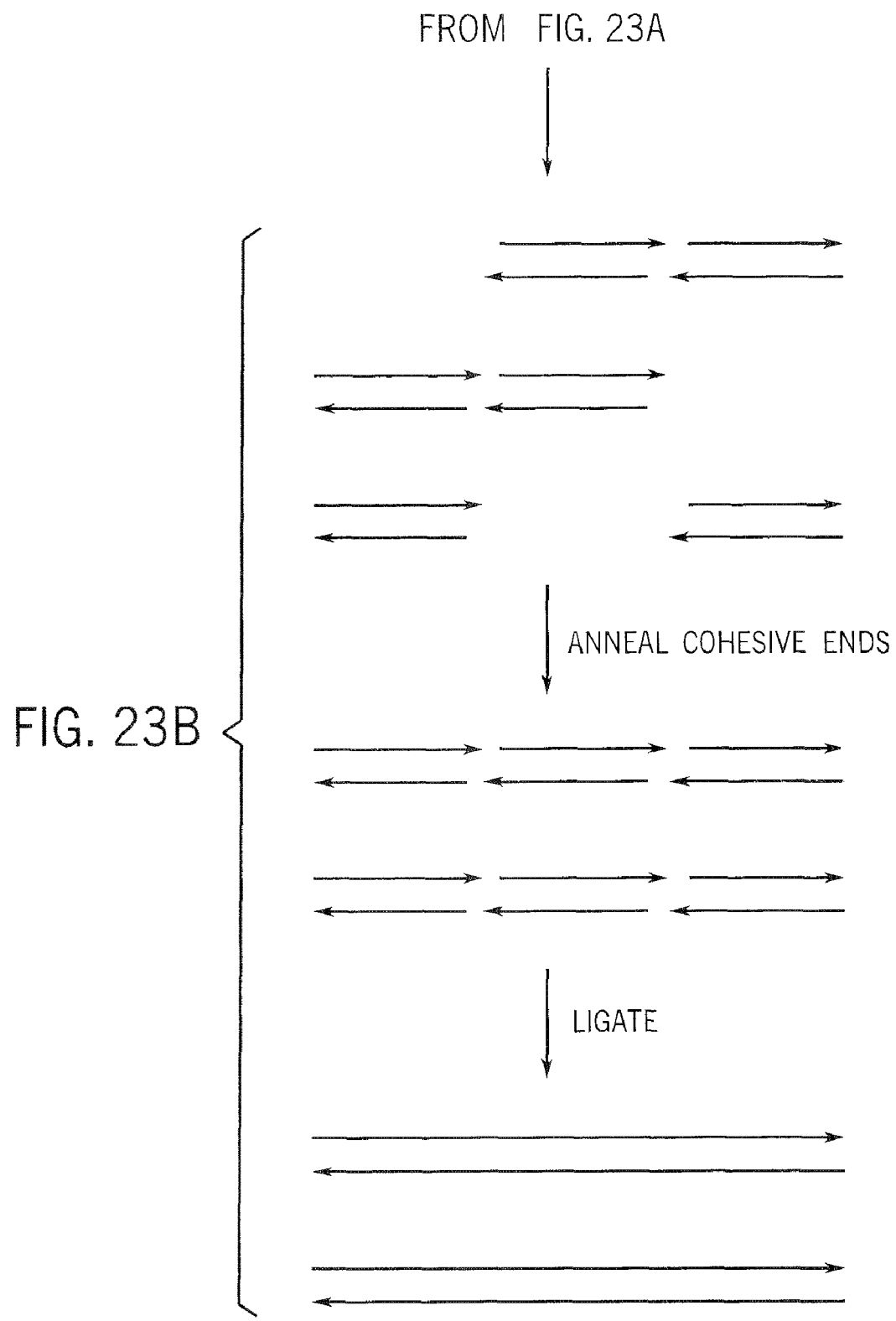

SEQUENCE LISTING

<160> NUMBER OF SEQ ID NOS: 14

<210> SEQ ID NO 1
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 1
atcggatcca ttt                                                        13

<210> SEQ ID NO 2
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 2
atcggatcca ttta                                                       14

<210> SEQ ID NO 3
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 3
atcggatcca t                                                          11

<210> SEQ ID NO 4
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 4
atcggatcca tt                                                         12

<210> SEQ ID NO 5
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 5
aaaatggatc cgat                                                       14

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
atcggatcca tttaccagg                                                  19

<210> SEQ ID NO 7
<211> LENGTH: 19
<212> TYPE: DNA

```
<213> ORGANISM: Artificial Sequence
<220> FEATURE:
<223> OTHER INFORMATION: Synthetic oligonucleotide

<400> SEQUENCE: 7
cctggtaaat ggatccgat                                               19

<210> SEQ ID NO 8
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 8
taaatggatc cgat                                                    14

<210> SEQ ID NO 9
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 9
taacctggtt acct                                                    14

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
accaggtaac ctggttacct                                              20

<210> SEQ ID NO 11
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 11
atcggatcca                                                         10

<210> SEQ ID NO 12
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 12
ggttggatcc gat                                                     13

<210> SEQ ID NO 13
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 13
atcggatcca accaggtaac ctggttacct ggttggatcc gat                    43
```

```
<210> SEQ ID NO 14
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 14
atcggatcca accagg                                                        16
```

METHODS FOR HIGH FIDELITY PRODUCTION OF LONG NUCLEIC ACID MOLECULES WITH ERROR CONTROL

CROSS-REFERENCE TO RELATED PATENT APPLICATIONS

This application is a divisional application of U.S. patent application Ser. No. 10/733,855, filed Dec. 10, 2003, now U.S. Pat. No. 7,932,025, issued Apr. 26, 2011, which claims the benefit under 35 USC 119(e) of U.S. Prov. Pat. Application Ser. No. 60/432,556, filed Dec. 10, 2002, both of which are incorporated herein by reference in their entirety.

FIELD OF THE INVENTION

This invention generally relates to nucleic acid synthesis, in particular DNA synthesis. More particularly, the invention relates to the production of long nucleic acid molecules with precise user control over sequence content. This invention also relates to the prevention and/or removal of errors within nucleic acid molecules.

BACKGROUND OF THE INVENTION

The availability of synthetic DNA sequences has fueled major revolutions in genetic engineering and the understanding of human genes, making possible such techniques as site-directed mutagenesis, the polymerase chain reaction (PCR), high-throughput DNA sequencing, gene synthesis, and gene expression analysis using DNA microarrays.

DNA produced from a user-specified sequence is typically synthesized chemically in the form of short oligonucleotides, often ranging in length from 20 to 70 bases. For methods and materials known in the art related to the chemical synthesis of nucleic acids see, e.g., Beaucage, S. L., Caruthers, M. H., *The Chemical Synthesis of DNA/RNA*, which is hereby incorporated by reference. Syntheses of longer oligonucleotides are possible, but the intrinsic error rate of each coupling step (typically 1-2%) is such that preparations of longer oligonucleotides are increasingly likely to be riddled with errors, and that the pure desired product will be numerically overwhelmed by sequences containing errors. Thus to produce longer DNA sequences, the molecule is not synthesized as a single long piece. Rather, current methods involve combining many shorter oligonucleotides to build the larger desired sequence, a process often referred to as "gene synthesis" (though the product need not be confined to a single gene).

Linear synthesis of nucleic acids may be accomplished using biological molecules and protecting groups. The most common linear synthesis techniques are based on solid-phase phosphoramidite chemistry. The 3'-phosphate is affixed to solid-phase support (typically controlled-pore glass beads, silicon substrates, or glass substrates), and an individual nucleotide of choice is added to a chain growing in the 3'-5' direction by means of a 5'-protecting group (typically an acid-labile or photo-cleavable protecting group).

In linear syntheses based on phosphoramidite chemistry, there are many potential sources of sequence error and oligonucleotide damage that are well documented. Most notably, the removal of the 5'-protecting group usually involves an acidic treatment that can remove the base, or in the case of photo-labile 5'-protecting group, require ultraviolet irradiation that can damage the nucleotide. The nucleotide may fail to incorporate into the growing strand because of insufficient reaction time. Nearly all organic and inorganic solvents and reagents employed in the process can chemically damage the growing nucleotide. Such sources of error ultimately limit the fidelity and length of the oligonucleotide, and furthermore, limit the fidelity and length of larger nucleic acids assembled from linearly synthesized strands. For methods and materials known in the art related to phosphoramidite nucleic acid synthesis see, e.g., Sierzchala, A. B., Dellinger, D. J., Betley, J. R., Wyrzykiewicz, Yamada, C. M., Caruthers, M. H., *Solid-Phase Oligodeoxynucleotide Synthesis: A Two-Step Cycle Using Peroxy Anion Deprotection*, J. AM. CHEM. SOC., 125, 13427-13441 (2003), which is hereby incorporated by reference.

Errors in gene synthesis are typically controlled in two ways: 1) the individual oligonucleotides can each be purified to remove error sequences; 2) the final cloned products are sequenced to discover if errors are present. In this latter case, the errors are dealt with by either sequencing many clones until an error-free sequence is found, using mutagenesis to specifically fix an error, or choosing and combining specific error-free sub-sequences to build an error free full length sequence.

Synthesizing a single gene has become commonplace enough that many companies exist to perform this task for a researcher. Single genes up to about 1000 base pairs (bp) are typically offered, and larger sequences are feasible, up to about 10,000 bp, for the construction of a single large gene, or a set of genes together. A recent benchmark was the production of the entire poliovirus genome, 7500 bp, capable of producing functional viral particles. These syntheses of long DNA products employ the methods described above, often aided by the large-scale production of oligonucleotides, such as with mutiplexed 48-, 96- or 384-column synthesizers, and using sample-handling robots to speed manipulations. For methods and materials known in the art related to gene synthesis, see e.g., Au., L., Yang, W., Lo., S., Kao, C., *Gene Synthesis by a LCR-Based Approach High-Level Production of Leptin-L45 Using Synthetic Gene in Escherichia Coli*, BIOCHEM. & BIOPHYS. RESEARCH COMM., 248, 200-203 (1998); Baedeker, M., Schulz, G. E., *Overexpression of a Designed 2.2 kb Gene of Eukaryotic Phenylalanine Ammonia-Lyase in Escherichia coli*, FEBS LETTERS 475, 57-60 (1999), Casimiro, D. R., Wright, P. E., Dyson, H. J., *PCR-based Gene Synthesis and Protein NMR Spectroscopy*, STRUCTURE, Vol. 5, No. 11, 1407-1412 (1997); Cello, J., Paul, A. V., Wimmer, E., *Chemical Synthesis of Poliovirus cDNA: Generation of Infectious Virus in the Absence of Natural Template*, SCIENCE, 297, 1016-1018 (2002); Kneidinger, B., Graninger, M., Messner, P., *Scaling Up the Ligase Chain Reaction-Based Approach to Gene Synthesis*, BIOTECHNIQUES, 30, 249-252 (2001); Dietrich, R., Wirsching, F., Opitz, T., Schwienhorst, A., *Gene Assembly Based on Blunt-Ended Double-Stranded DNA-Molecules*, BIOTECH. TECHNIQUES, Vol. 12, No. 1, 49-54 (1998); Hoover, D. M., Lubkowski, J., *DNAWorks: An Automated Method for Designing Oligonucleotides for PCR-based Gene Synthesis*, NUCLEIC ACIDS RESEARCH, Vol. 30, No. 10, 1-7 (2002); Stemmer, W. P. C., Crameri, A., Ha, K. D., Brennan, T. M., Heyneker, H. L., *Single-Step Assembly of a Gene and Entire Plasmid from Large Numbers of Oligodeoxyribonucleotides*, GENE, 164, 49-53 (1995); Withers-Martinez, C., Carpenter, E. P., Hackett, F., Ely, B., Sajid, M., Grainger, M., Blackman, M. J., *PCR-Based Gene Synthesis as an Efficient Approach for Expression of the A+T-Rich Malaria Genome*, PROTEIN ENG., Vol. 12, No. 12, 1113-1120 (1999); and *Venter Cooks Up a Synthetic Genome in Record Time*, SCIENCE, 302, 1307 (2003) all of which are hereby incorporated by reference. For patents and patent applications related to gene synthesis, see e.g., U.S. Pat. Nos. 6,521,453 and 6,521,427, and U.S. Pat. App.

Pub. Nos. 20030165946, 20030138782, and 20030087238, all hereby incorporated by reference.

As the goals of genetic engineers become more complex and larger in scale, these methods become prohibitive in terms of the cost, time, and effort involved to produce longer sequences and correct the subsequent errors. For example, a fee may be $5 per by for a 500 bp sequence, with a waiting time of 2-4 weeks, whereas even the most rapid portion of the poliovirus synthesis required several months and tens of thousands of dollars (the project overall required two years and over $100,000). A technology which makes this process both faster and more affordable would be a tremendous aid to researchers in need of very long DNA molecules.

Some examples of work which would benefit:

1) Vaccine trials (modest DNA length, but many variants): in producing proteins for use in vaccine trials, a large number of variant protein sequences are often examined. The number of options explored is typically limited by the number of variants that can be produced. The lengths of the DNA molecules encoding such proteins might be in the range of about 100 bp to about 2000 bp, or longer, depending on the protein. One of ordinary skill in the art will understand that the length of a DNA molecule may vary greatly depending on the protein product desired.

2) Gene therapy (intermediate DNA length): retroviral vectors used for gene therapy might range from about 20,000 to about 50,000 bp. The process of constructing these vectors also limits the number and complexity of variants which can be tested in the laboratory.

3) Bacterial engineering (greatest DNA length, genomic synthesis): currently, changes made to a bacterial organism are attempted one gene at a time, a painstaking process when several changes are desired. In the case of engineering a bacterium to perform a task, such as waste detoxification or protein production, a large number of intricate changes may be required. If the complete genome of the desired bacterium could be generated easily de novo, a great deal of time and effort could be saved, and new areas of research would be made possible. Bacterial genomes range from several hundred kilobases to many megabases. One of ordinary skill in the art will understand that the size of bacterial genomes varies greatly depending on the bacterium in question.

The fundamental challenges of the current technology:

1) Scaling: as the size of the desired sequence grows, the production time and costs involved grow linearly, or worse. An ideal method would involve smaller amounts of reagents, shorter cycle times for oligonucleotide synthesis, a greatly improved parallelization of the synthesis process used to provide the oligonucleotides, and/or an improved process for the assembly of oligonucleotides into larger molecules.

2) Errors: with the production of larger DNA sequences, expected per base error rates will essentially guarantee that conventional methods will yield sequences containing errors. These errors will require more effective techniques than the current control procedures described above.

SUMMARY OF THE INVENTION

The present invention provides methods for the error-free production of long nucleic acid molecules with precise user control over sequence content. In a preferred embodiment of the invention, long error-free nucleic acid molecules can be generated in parallel from oligonucleotides immobilized on a surface, such as an oligonucleotide microarray. The movement of the growing nucleic acid molecule can be controlled through the stepwise repositioning of the growing molecule. Stepwise repositioning refers to the position of the growing molecule as it interacts with the oligonucleotides immobilized on the surface. One aspect of the invention allows for the synthesis of nucleic acids in a parallel format through the use of a ligase or polymerase reaction. In another aspect of the invention, the oligonucleotides may also be detached from their support and manipulated by, for example, a microfluidic device for the purpose of assembly into larger molecules. Regarding parallel DNA arrays, it is important to note that a single nucleotide may be synthesized using the parallel arrays, and then amplified by techniques well known in the art, such as but not limited to, polymerase chain reaction.

In another aspect of the invention, the synthesis of a long nucleotide chain may be accomplished in parallel starting from a set of many redundantly overlapped oligonucleotides. Synthesis relies on annealing complementary pairs of oligonucleotides and extending them to produce longer oligonucleotide segments, until the full-length sequence is produced. The majority of the oligonucleotide sequence is used to generate the complementary overlap, improving the chance of the two strands annealing. This approach guards against the failed synthesis of any one distinct oligonucleotide sequence, as a less complementary pair of oligonucleotides may still anneal under the appropriate conditions and produce a full length nucleotide sequence. In another aspect of the invention, long nucleotide sequences may contain one or more regions containing sites specifically designed to facilitate the joining of separate molecules. These sequences can be sites for specific endonuclease restriction and subsequent ligation, homologous recombination, site-specific recombination, or transposition.

A preferred embodiment of the invention provides a method for the synthesis of single-stranded DNA with various 3'-phosphate protecting groups, such as but not limited to, peptide, carbohydrate, diphosphate, or phosphate derivative 3'-phosphate protecting groups. After an addition to the nascent DNA strand by a capped nucleotide or oligonucleotide, a protease or phosphotase cleaves the bond between the capping group and the most recently added nucleotide. DNA polymerase or nucleotide ligase can be used to add a 3' capped nucleotide or oligonucleotide to the 3' end of the nascent strand. DNA ligase can also be used to add a 5' capped nucleotide or oligonucleotide to the 5' end of the nascent strand.

Another preferred embodiment of the invention provides a method for the synthesis of a double-stranded DNA with an oligonucleotides capping group. The capping group is comprised of a nucleotide or short oligonucleotide that can be cleaved from the nascent strand by a restriction enzyme. After the addition of a capped nucleotide or oligonucleotide, a restriction enzyme which recognizes the capping nucleotide sequence will cleave the fragment 3' to the newly added nucleotide. Thus, the desired nucleotide will remain on the nascent strand. This procedure is repeated to create a specific oligonucleotide sequence. Different restriction enzymes and corresponding capping nucleotides or sequence redesign may be required for the creation of desired oligonucleotides in order to prevent sequence recognition in the nascent strand.

Yet another preferred embodiment of the invention provides a method for the synthesis of single-stranded and/or double-stranded DNA using oligonucleotide hairpin-loops as heat-removable protecting groups and/or PCR primers. Oligonucleotides with secondary conformational structures, such as DNA hairpin-loops (also termed stem-loops, and molecular beacons), can also be used as protecting groups. Gentle heating is an improved method of deprotection over enzymatic removal because heat distributes more quickly and uniformly than enzymes because the enzymatic removal rate is diffusion-limited, and gentle heating is a lower-cost resource than restriction enzymes.

The present invention also provides methods for detecting and correcting errors that arise in the process of constructing long nucleic acid molecules. A preferred embodiment of the invention utilizes a force-feedback system using magnetic and/or optical tweezers, either separately or in combination. Using this system, double or single-stranded DNA is grown off a solid-phase support using one or a combination of the aforementioned DNA synthesis methods. The solid-phase support is magnetic in nature and held in a fixed equilibrium position by applying an electric field and magnetic field gradient created by the magnetic tweezers that opposes the electrophoretic force. As oligonucleotides are annealed to the growing strand, the negatively charged phosphate backbone adds charge to the bead-strand complex. However, the added oligonucleotide adds essentially no mass or surface area to the complex. Assuming the zeta-potential of the dielectric bead is constant, the addition of an oligonucleotide strand is the only contribution to the increase in electrophoretic force felt by the particle. The increased electrophoretic moves the bead from its equilibrium position, and the magnetic field gradient must be increased to restore the bead to its equilibrium position. Optically determined bead velocity and restoration force correspond to the number of bases added. Therefore, the length of the added strand can be ensured to be correct. Optical detection can be by way of a CCD or split-photodiode. This scheme in can also be modified to employ optical tweezers to apply an optical force rather than a magnetic force. Furthermore, this method can utilize coupled magneto-optical tweezers. The optical and magnetic forces can be created simultaneously or independently of one another.

Another preferred embodiment of the invention also provides methods for detecting and correcting errors that arise in the process of constructing long nucleic acid molecules. A preferred embodiment of the invention utilizes electrophoresis as a force-feedback system. In this scheme, a single strand of DNA is synthesized on a fluorescent bead functionalized with a single phosphate group, and electrophoretically passed through a medium with excess ATP, kinase, and ligase. The rate of motion of the bead is monitored and used as the feedback mechanism. First, excess ATP is passed through the medium simultaneously (with the bead). Excess ATP will pass through the medium much faster than the bead. The kinase will catalyze the formation of a triphosphate on the bead using ATP. When this occurs, the rate of motion of the bead will change, due to a change in the charge/mass ratio. The measurement of this change thus serves to indicate a successful reaction. Once the triphosphate has formed on the bead, excess free nucleotide is passed through the medium. These small molecules will pass through the medium much faster than the bead. DNA ligase will catalyze the addition of the nucleotide, releasing a diphosphate. The rate of motion of the bead is reduced because the loss of the diphosphate decreases the charge/mass ratio. This serves as feedback for base addition. Multiple-nucleotide addition in this step should not occur because after one addition, there is no triphosphate present in the system, which DNA ligase needs to add the base. Once a successful nucleotide addition is detected, more ATP is introduced into the system and the described cycle repeats.

Another preferred embodiment of the invention uses heat as an additional feedback and error correction mechanism in force feedback systems. Prior to enzymatic ligation, the melting point of the small oligonucleotide in contact with the growing nucleic acid strand will be lowered if base-pair mismatches occur. The controlled application of heat after detected annealing can provide additional feedback about base-pair mismatches. If the oligonucleotide dehybridizes from the growing strand as the melting point is approached, but not reached, a base-pair mismatch is detected when a decrease in magnetophoretic force, or increase in electrophoretic force is required to keep the bead in equilibrium. Because the erroneous strand is removed by heat, this feedback process is also an error-correction mechanism.

Another preferred embodiment of the invention utilizes exonuclease activity for nucleotide removal for error-correction in force-feedback systems. This type of error-correction is particular useful for correcting errors after enzymatic ligation of an erroneous strand. Whereas it would be extremely difficult to control the exact number of nucleotides that exonuclease removes from the 3'-end of a growing strand of nucleic acid, that level of control is not required in the methods reported herein because the feedback systems allow for the length of the strand to be determined after the error-correction steps. Therefore, if too many nucleotides are initially removed, they may be added back later.

A novel aspect of the invention accounts for the potential that an error may occur that cannot be detected or corrected by the use of parallel detection. The parallelization of single-molecule systems is desirable to ensure that the process is successful and also allows for various nucleic acids of different sequences to be synthesized simultaneously. Parallel single-molecule systems may use arrays of light sources and detectors. Parallel single-molecule systems using only one light source and detector are also possible.

Parallel detection may also be performed without the use of arrays. Single-molecule systems in which the solid-phase supports have negligible interactions can be parallelized without the use of arrays. For example, optical tweezers may be employed in the single-molecule system as described in FIG. 9B. Multiple beads in the same microscope field of view are trapped by rastering the laser beam using an acoustical-optical modulator (AOM). In another example, multiple beads may be tracked using only one CCD camera. The ability to control beads independently is not available in this system. However, beads with erroneous nucleic acids can be tracked and discarded after the entire process is complete.

Another novel aspect of this invention provides methods for the microfabrication of electromagnet arrays. The area density of electromagnet arrays is maximized if the electromagnets are fabricated by bulk-microfabrication techniques. First, a layer of diagonal metal wires are lithographically defined and deposited on a silicon substrate. Bond pads are also defined in this first step. Then, a film of soft magnetic material is lithographically designed and deposited over a portion of the metal lines. A second layer of metal lines are lithographically defined and deposited over the magnetic film layer to complete the microfabrication of in-plane microelectromagnets.

A preferred embodiment of the invention provides a method for error detection and correction using a nanopore device for single-molecule synthesis with feedback using fluorescent 5' protecting groups. DNA is synthesized on a non-fluorescent solid support and passes through a sub-micron size opening, known as a nanopore, with a fluorescence detector. The bead can be directed to one of two channels by a switch, depending on whether a successful addition has occurred. After the coupling step and removal of excess reagents, the bead is passed through the pore. If no fluorescence is detected, either the coupling reaction was unsuccessful, or it was successful but not detected. The bead is directed back into the device for another coupling step. Because the 5' end of the growing strand is protected, a redundant coupling step will not result in multiple-base addition.

Another preferred embodiment of the invention provides a method for error detection and correction using uses a nanopore device for single-molecule synthesis with feedback using fluorescent 5' protecting groups. Monitoring the deprotection of the 5' group is necessary to eliminate deletion errors. In this device, the growing strand is deprotected, and the wash is flowed through the nanopore, not the bead, and the nanopore only leads to one channel. If no fluorescence is detected in the wash, then the strand was not deprotected, or it was successfully deprotected but the fluorescent protecting group was not detected. The wash is constantly recycled until a fluorescent group is detected. Because there are no free nucleotides (only the growing strand) in this device, no addition error can occur by redundant 5' deprotection steps.

A novel aspect of the invention allows for independent control of a cluster of superparamagnetic beads by an electric field and opposing magnetic field gradient. The electrophoretic force moves the beads in one direction, and the magnetic field gradient moves the beads in the opposite direction.

The present invention provides methods utilizing biological molecules for detecting and correcting errors that arise in the process of constructing long nucleic acid molecules. In one preferred embodiment of the invention, mismatch recognition can be used to control the errors generated during oligonucleotide synthesis, gene assembly, and the construction of nucleic acids of different sizes. One of ordinary skill in the art will understand mismatch to mean a single error at the sequence position on one strand which gives rise to a base mismatch (non-complementary bases aligned opposite one another in the oligonucleotide), causing a distortion in the molecular structure of the molecule. In one aspect of the invention, mismatch recognition is achieved through the use of mismatch binding proteins (MMBP). The MMBP binds to a mismatch in a DNA duplex; the MMBP-bound DNA complex is then removed using methods of protein purification well known to those having ordinary skill in the art. Another aspect of the invention allows for separation of the MMBP-bound DNA complex using a difference in mobility, such as by size-exclusion column chromatography or gel electrophoresis. For methods and materials known in the art related to DNA mismatch detection, see e.g., Biswas, I., Hsieh, P., *Interaction of MutS Protein with the Major and Minor Grooves of a Heteroduplex DNA*, JOURNAL OF BIO. CHEMISTRY, Vol. 272, No. 20, 13355-13364 (1997); Eisen, J. A., *A Phylogenomic Study of the MutS Family of Proteins*, NUCLEIC ACIDS RESEARCH, Vol. 26, No. 18, 4291-4300 (1998); Beaulieu, M., Larson, G. P., Geller, L., Flanagan, S. D., Krontiris, T. G., *PCR Candidate Region Mismatch Scanning: Adaption to Quantitative, High-Throughput Genotyping*, NUCLEIC ACIDS RESEARCH, Vol. 29, No. 5, 1114-1124 (2001); Smith, J., Modrich, P., *Removal of Polymerase-Produced Mutant Sequences from PCR Products*, PROC. NATL. ACAD. SCI, 94, 6847-6850 (1997); Smith, J., Modrich, P., *Mutation Detection with MutH, MutL, and MutS Mismatch Repair Proteins*, PROC. NATL. ACAD. SCI, 93, 4374-4379 (1996); and Bjornson, K. P., Modrich, P., *Differential and Simultaneous Adenosine Di- and Triphosphate Binding by MutS*, JOURNAL OF BIO. CHEMISTRY, Vol. 278, No. 20, 18557-18562 (2003), all of which are hereby incorporated by reference. For patents relating to DNA mismatch repair systems, see e.g., U.S. Pat. Nos. 6,008,031, 5,922,539, 5,861,482, 5,858,754, 5,702,894, 5,679,522, 5,556,750, 5,459,039, all hereby incorporated by reference.

In another aspect of the invention, a MMBP can be irreversibly complexed to an error containing DNA sequence by the action of a chemical crosslinking agent. The pool of DNA sequences is then amplified, but those containing errors are blocked from amplification, and quickly become outnumbered by the increasing error-free sequences. In another aspect of the invention, DNA methylation may be used for strand-specific error correction. Methylation and site-specific demethylation are employed to produce DNA strands that are selectively hemi-methylated. A methylase is used to uniformly methylate all potential target sites on each strand, which are then dissociated and allowed to re-anneal with new partner strands. A MMBP with demethylase complex is applied, which binds only to the mismatch. The demethylase portion of the complex removes methyl groups only near the site of the mismatch. A subsequent cycle of dissociation and annealing allows the demethylated error-containing strand to associate with a methylated error free strand. The hemi-methylated DNA duplex now contains all the information needed to direct the repair of the error, employing the components of a DNA mismatch repair system.

In another aspect of the invention, local DNA on both strands at the site of a mismatch may be removed and resynthesized to replace the mismatch error. For example, a MMBP fusion to a non-specific nuclease (N) can bind to a mismatch site on DNA, forming a MMBP-nuclease DNA complex. The complex can then direct the action of the nuclease to the mismatch site, and cleave both strands. Once the break is generated, homologous recombination can be employed to use other, error-free strands as template to replace the excised DNA. Other mechanisms of DNA synthesis well known in the art, such as strand invasion and branch migration, may also be used to replace the excised DNA. Alternatively, a polymerase can be employed to allow broken strands to reassociate with new full-length partner strands, synthesizing new DNA to replace the error. In another aspect of the invention, the MMBP-nuclease-excised DNA complex can be physically separated from the remaining, error free DNA using various techniques well known in the art. For methods and materials known in the art related to nucleases and fusion proteins, see e.g., Kim, Y., Chandrasegaran, S., *Chimeric Restriction Endonucleases*, PROC. NATL. ACAD. SCI, 91, 883-887 (1994); Kim, Y., Shi, Y., Berg, J. M., Chandrasegaran, S., *Site-Specific Cleavage of DNA-RNA Hybrids by Zinc Finger/FokI Cleavage Domain Fusions*, GENE, 203, 43-49 (1997); Li, L., Wu, L. P., Chandrasegaran, S., *Functional Domains in Fok I Restriction Endonuclease*, PROC. NATL. ACAD. SCI, 89, 4275-4279 (1992); Kim, Y., Lowenhaupt, K., Schwartz, T., Rich, A., *The Interaction Between Z-DNA and the Zab Domain of Double-Stranded RNA Adenosine Deaminase Characterized Using Fusion Nucleases*, JOURNAL OF BIO. CHEMISTRY, Vol. 274, No., 27, 19081-19086 (1999); Ruminy, P., Derambure, C., Chandrasegaran, S., Salier, J., *Long-Range Identification of Hepatocyte Nuclear Factor-3 (FoxA) High and Low-Affinity Binding Sites with a Chimeric Nuclease*, J. MOL. BIOL., 310, 523-535 (2001); Wah, D. A., Bitinaite, J., Schildkraut, I., Aggarwal, A. K., *Structure of FokI has Implications for DNA Cleavage*, PROC. NATL. ACAD. SCI, 95, 10564-10569 (1998); and Wah, D. A., Hirsch, J. A., Dorner, L. F., Schildkraut, I., Aggarwal, A. K., *Structure of the multimodular endonuclease FokI bound to DNA*, NATURE, 388, 97-100 (1997) all of which are hereby incorporated by reference.

These and other aspects of the present invention will become evident upon reference to the following detailed description. Additionally, various references are set forth herein. Each of these references is hereby incorporated by reference in its entirety as if each was individually noted for incorporation.

BRIEF DESCRIPTION OF THE DRAWINGS

FIGS. 8A-C show an embodiment of the invention employing an all-biological synthetic strategy for the synthesis of double-stranded DNA using oligonucleotide hairpin-loops as heat-removable protecting groups.

FIG. 10 shows an aspect of the invention employing force-feedback, in this case electrophoresis, in order to screen for and correct errors.

FIGS. 16A-C show an embodiment of the invention for removing error sequences using mismatch binding proteins (MMBP). An error in a single strand of DNA causes a mismatch in a DNA duplex, which is selectively bound by a MMBP and separated from error-free DNA by methods known in the art such as by affinity capture or mobility differences.

FIGS. 21A and 21B show an aspect of the invention for removing and correcting error sequences using a MMBP fusion to a non-specific nuclease and both strand invasion and branch migration to synthesize the error-free portions of the nucleotide sequence.

FIGS. 23A and B show an aspect of the invention for removing and correcting error sequences using a non-specific endonuclease to cut the molecule into shorter strands, binding error containing strands with MMBP, separating error containing MMBP complexed strands, and annealing and ligating cohesive ends.

DETAILED DESCRIPTION OF THE INVENTION

Figure 1A:
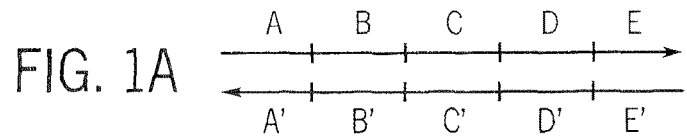
FIGS. 1A-F show an embodiment of the invention for generating long DNA sequences from oligonucleotides immobilized on a surface, such as an oligonucleotide microarray.

Part I. Production of Very Long Strands of Nucleic Acids

Many protocols exist for assembling oligonucleotides into larger molecules of nucleic acid. These include ligase-based and polymerase-based methods. Some of these methods combine all the necessary oligonucleotides into a single pool for assembly (sometimes referred to as "shotgun" assembly) while others assemble subsets of the oligonucleotides into larger sequences, and then combine these sequences to yield the final full length product. Additionally, the fidelity of the initial library of short oligonucleotides often limits the fidelity of the full-length product. However, the production and manipulation of oligonucleotides needed to produce molecules containing more than a few thousand bases proves an arduous effort. This disclosure details methods for employing large numbers of oligonucleotides to efficiently generate molecules of nucleic acid on this length scale, and much greater length scales as well. These methods can be applied to the generation of an extremely long molecule of nucleic acid, such as in the case of a bacterial genome, or to the parallel production of many different molecules of nucleic acid of intermediate length, such as many variants of a single gene. For methods and materials known in the art related to parallel production of biopolymers, see e.g., Lipshutz, R. J., Fodor, S. P. A., Gingeras, T. R., Lockhart, D. J., *High Density Synthetic Oligonucleotides Arrays*, NATURE GENETICS SUPP., 21, 20-24 (1999); Pellois, J. P., Zhou, X., Srivannavit, O., Zhou, T., Gulari, E., Gao, X., *Individually Addressable Parallel Peptide Synthesis on Microchips*, NATURE BIOTECHOL., 20, 922-926 (2002); Gao, X., LeProust, E., Zhang, H., Srivannavit, O., Gulari, E., Yu, P., Nishiguchi, C., Xiang, Q., Zhou, X., *A Flexible Light-Directed DNA Chip Synthesis Gated by Detrotection Using Solution Photogenerated Acids*, NUCLEIC ACIDS RES., Vol. 29, No. 22, 4744-4750 (2001); and Singh-Gasson, S., Green, R. D., Yue, Y., Nelson, C., Blattner, F., Sussman, M. R., Cerrina, F., *Maskless Fabrication of Light-Directed Oligonucleotide Microarrays Using a Digital Micromirror Array*, NATURE BIOTECHOL., 17, 974-978 (1999) all of which are hereby incorporated by reference.

According to the invention, the methods described herein can be applied to 1) multiple kinds of nucleic acids (including ribonucleic acid, peptide-nucleic acid, locked-nucleic acid, and any combinations thereof); and 2) other types of polymers, such as, but not limited to, RNA, PNA, LNA, etc. However, these examples are to be considered in all respects illustrative rather than limiting on the invention described herein. The examples given refer to, but are not limited to, deoxyribonucleic acid (DNA). According to the invention, the methods described herein may be performed in vivo or in vitro.

FIGS. 1A-F display a process of the invention for generating long DNA sequences from oligonucleotides immobilized on a surface, such as an oligonucleotide microarray. Such arrays are currently generated by a variety of synthetic approaches, including photolabile deprotection, photo-induced acid-labile deprotection, electrically-induced acid-labile deprotection, and inkjet printing of reagents. The number of different oligonucleotides that can be produced in microarray form is quite large. Some arrays may hold about 20,000 distinct locations, each with a different oligonucleotide sequence. The highest density arrays can contain about 400,000 distinct locations per square centimeter. For an array of 50-mer oligonucleotides, this would correspond to 20 million bases, roughly four times the genome size of many common bacteria.

FIG. 1A. The desired double-stranded DNA sequence to be produced, labeled in sections. Arrowheads indicate the 3' end of each DNA strand. Complementary sections of the top and bottom strand are indicated as A, A', and so forth.

Figure 1B:
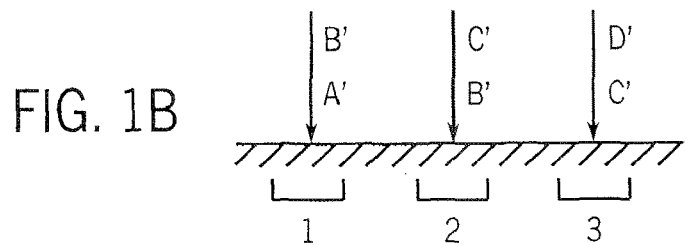

FIG. 1B. A portion of an oligonucleotide microarray containing all the oligonucleotide sequences necessary for generating the sequence of FIG. 1A. Each region of the microarray (1, 2, 3, ...) contains oligonucleotides of a single, distinct sequence, with only a single strand from each shown for clarity. The oligonucleotides are covalently attached to the surface indicated, and are immersed in a solution suitable for performing enzymatic reactions such as PCR.

Figure 1C:
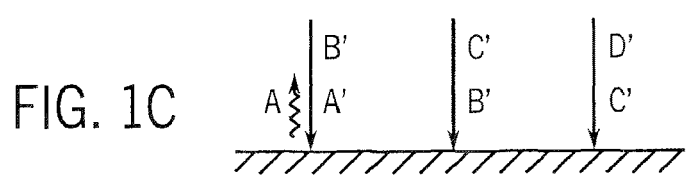

FIG. 1C. An oligonucleotide primer equivalent to the sequence of DNA section "A" is added to the solution. The sequence of this oligonucleotide is complementary to that of immobilized oligonucleotide 1 (which contains sequences A' and B') and will selectively hybridize to the A' region of that oligonucleotide, producing a region of double-stranded DNA.

Figure 1D:
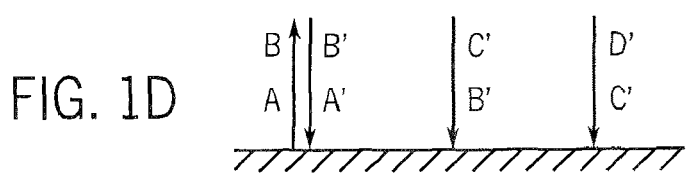

FIG. 1D. The action of a DNA polymerase, such as those used for PCR (e.g. Taq, Pwo, Pfu) is used to extend the primer, adding sequence B.

Figure 1E:
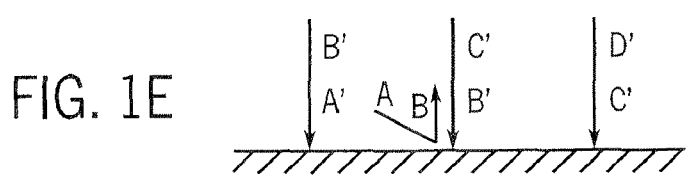

FIG. 1E. Sequence AB is dissociated from oligonucleotide 1 (A'B'). This can be accomplished using conventional PCR thermocyclers adapted for flat supports (typically used with glass slides for in situ PCR) The free AB sequence is moved through the solution (by the action of diffusion, bulk liquid flow, electrophoresis, or using attached magnetic particles) to the site of oligonucleotide 2 (containing sequence B'C').

Figure 1F:
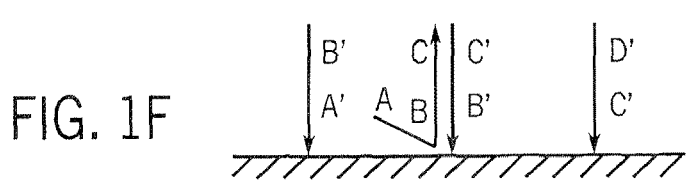

FIG. 1F. As in FIG. 1D, a DNA polymerase extends sequence AB to yield sequence ABC. Repetition of the steps of dissociation, annealing, and extension are used to produce the DNA sequence of desired length.

One advantage of the method shown in FIGS. 1A-F is the ability to track the progress and growth of the product by fluorescence. The free oligonucleotide corresponding to the 5' end of the sequence can include a fluorescent group at the 5' terminus. As the growing chain anneals to different spots on the microarray, regions of high concentration of the fluorescent group (where the free oligonucleotide is bound) are detected by fluorescence microscopy. Thus, the progress of the growing chain can be monitored. For example, fluorescence at oligonucleotide spot 3 indicates that the growing free DNA chain must contain at least sequence ABC in order to anneal. This monitoring is especially useful in the case of potential mis-annealing between sequences which are similar, but not the intended (perfect) match. In this case, the presence of a fluorescent spot at an unexpected location shows which sequence the free oligonucleotide has annealed to.

Another aspect of this invention is the stepwise repositioning of the growing DNA chain as a means to control the movement of some additional component. Referring to FIGS. 1A-F, for the first cycle of annealing, the attached component will only be present at spot 1. Following strand extension by polymerase, the sequence attached to the component now has the sequence AB. In the second cycle of annealing, this complex will advance no further than spot 2, and so forth. The attached growing chain will still also have affinity for spot 1, and will be partially localized there as well. However, the component and attached DNA chain can be "chased" through the spot locations by adding an excess of free oligonucleotide sequence A in a later cycles. For example, adding excess A in cycle 2 means that free oligonucleotide A will compete with the AB-attached component to anneal to spot 1 (in essence, flushing the AB-attached component away from this site), but only the AB-attached component will have affinity for site 2 (via the interaction between B-B' sequences).

In a preferred embodiment of the invention, the oligonucleotides to be used will be synthesized in a parallel format, such as in an oligonucleotide microarray. The oligonucleotides will be detached from their support and manipulated, for example, by a microfluidic device for the purpose of assembly into larger molecules of nucleic acid. The oligonucleotides can be detached selectively or in groups. Oligonucleotides produced in this device could also be used for other processes affecting the amount and quality of the final product: examples include affinity purification, amplification, sequencing, and mutagenesis. Means to manipulate oligonucleotides and other nucleic acid molecules in this device are well known in the art, and include but are not limited to, passive diffusion, liquid flow, electrophoresis, attachment to a movable solid support such as a magnetic bead, and affinity for nucleic acid or other molecules.

FIGS. 2A-G show a process of the invention for generating long DNA sequences from oligonucleotides synthesized on a surface, and then detached from that surface.

Figure 2A:
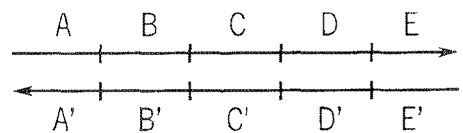
FIGS. 2A-G show an aspect of the invention for generating long DNA sequences from oligonucleotides synthesized on a surface, and then detached from that surface into solution.

FIG. 2A. The desired DNA sequence to be produced, labeled in sections. As in FIG. 1, arrowheads indicate the 3' end of each DNA strand. Complementary sections of the top and bottom strand are indicated as A, A', and so forth.

Figure 2B:
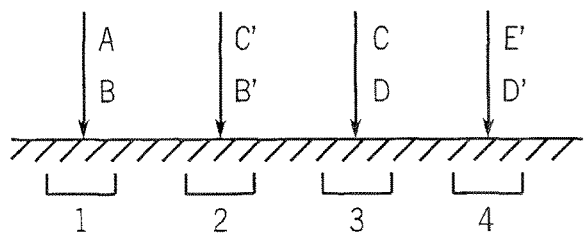

FIG. 2B. A portion of an oligonucleotide microarray containing all the DNA sequences necessary for producing the full length sequence of FIG. 2A. Each region (1, 2, 3, ...) contains oligonucleotides of a single, distinct sequence, with only a single strand of each shown for clarity. The oligonucleotides are covalently attached to the surface via a covalent linker that can be cleaved (using chemistry similar to that of conventional oligonucleotide synthesis, in which the final product is cleaved from a solid support on a column, or by other methods such as photolabile chemistry).

Figure 2C:
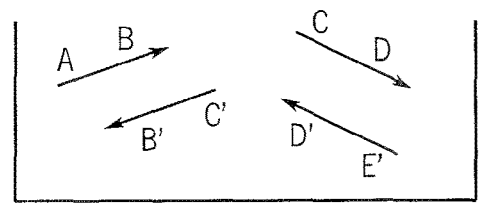

FIG. 2C. The oligonucleotides are cleaved from the surface, releasing them into solution.

Production of larger DNA sequences can proceed using either the polymerase chain reaction (PCR, using a thermostable DNA polymerase) or a ligase reaction (including LCR, ligase chain reaction, using a thermostable DNA ligase). A variety of related gene synthesis approaches are also possible at this step.

Figure 2D:
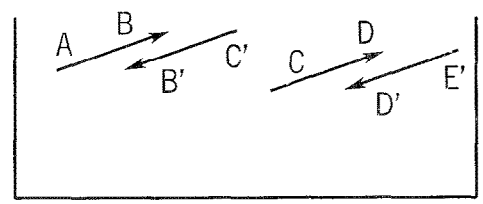

FIG. 2D. The complementary regions of the oligonucleotides associate to create regions of double-stranded DNA. (Only some of these combinations are shown for clarity.) This process can occur using the oligonucleotides directly as released from the original surface, or after a concentration step using electrophoresis, osmotic filtration, or simple evaporation. A microfluidic device can be employed to aid in the manipulation, combination, and concentration of oligonucletides. Such a use is particularly desirable in the case of producing a set of distinct and separate DNA sequences from a single microrray, such as producing many variants of the same gene. Such a use is also particularly desirable for the manipulation of DNA sequences for DNA computing. For methods and materials known in the art related to microfluidic devices, see e.g., Lagally, E. T., Medintz, I., Mathies, R. A., *Single-Molecule DNA Amplification and Analysis in an Integrated Mircrofluidic Device*, ANAL. CHEM., 73, 565-570 (2001), which is hereby incorporated by reference.

Figure 2E:
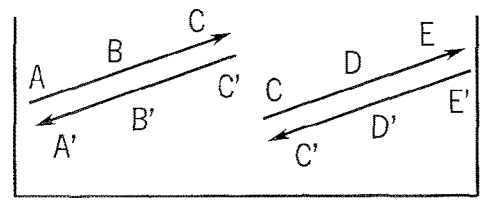

FIG. 2E. A DNA polymerase extends the 3' ends of the oligonucleotides, producing larger DNA duplexes.

Figure 2F:
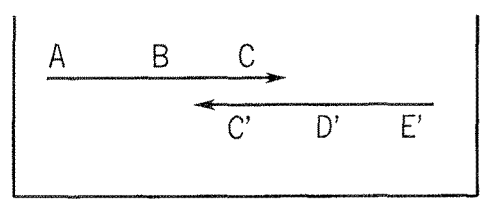

FIG. 2F. DNA duplexes are dissociated and allowed to reanneal. One of the resulting new duplexes is shown.

Figure 2G:
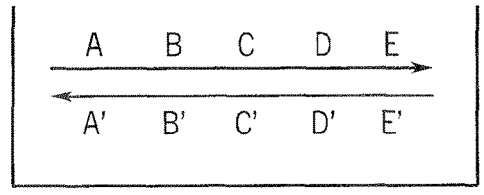

FIG. 2G. DNA polymerase again extends the 3' ends of the annealed oligonucleotides, producing still larger DNA duplexes. The process of dissociation, annealing, and extension is then repeated over multiple cycles, allowing increasingly longer DNA sequences to be assembled, producing the desired target sequence.

In conventional gene assembly, oligonucleotides are synthesized to represent the complete sequence, with overlaps designed between pairs for annealing prior to extension by a DNA polymerase or ligation by a DNA ligase. As the size of the target sequence grows, so does the number of oligonucleotides needed to assemble it. As the number of oligonucleotides grows, the potential for oligonucleotides to partner with incorrect strands also increases. This problem can be addressed partially by employing higher temperatures for the annealing conditions, minimizing the chance of mis-partnering. This approach generally requires longer overlaps, and thus longer oligonucleotides. For an oligonucleotide of a given length, up to half that length is used to form each overlap. However, using a synthesis method of the invention with the scale of synthesis possible on a single microarray (tens of thousands or more of oligonucleotides of distinct sequences), it becomes practical to use an even higher proportion of the oligonucleotides to form each overlap. Thus the maximal specificity of annealing is achieved in this aspect of the invention by including many oligonucleotides of closely spaced sequence. At the same time, the length of the oligonucleotide may be kept to a minimum, which reduces some types of errors inherent in oligonucleotide synthesis. For methods and materials known in the art related to the synthesis of nucleic acids using microarrays, see e.g., McGall, G. H., Barone, A. D., Diggelmann, M., Fodor, S. P. A., Gentalon, E., Ngo, N., *The Efficiency of Light-Directed Synthesis of DNA Arrays on Glass Substratesi*, J. AM. CHEM. SOC., Vol. 119, No. 22, 5081-5090 (1997), which is hereby incorporated by reference.

FIGS. 3A-D show the synthesis of a large DNA molecule starting from a set of many redundantly overlapped oligonucleotides. As in FIGS. 2A-G, assembly relies on annealing complementary pairs of oligonucleotides and extending them to produce longer segments of DNA, until the full-length sequence is produced. However, in this case, the majority of the oligonucleotide sequence is used to generate the complementary overlap, improving the maximum possible specificity of annealing. Though the first polymerase extensions only produce slightly larger pieces of DNA, later growth steps are still exponential. Also, sometimes a particular oligonucleotide synthesis may fail, or be especially inefficient. For methods and materials known in the art related to nucleotide synthesis involving overlapped oligonucleotides see, e.g., European Patent Application EP 1314783A1 titled *Nukleinsaure-Linker and deren Verwendung in der Gensynthese* assigned to Sloning BioTechnology GmbH, which is hereby incorporated by reference.

This approach provides "insurance" against the failure of the synthesis of any one distinct oligonucleotide sequence. For example, in FIGS. 2A-G, a failure to produce oligonucleotide sequence CD would result in an inability to produce the longer CDE and ABCDE strands. In contrast, removal of any one oligonucleotide shown in FIG. 3B does not prevent assembly of the full-length molecule. Thus, the many possible overlaps ensure that even if one oligonucleotide (such as oligonucleotide 2) were removed, the full-length assembly will still be achievable, because the full-length sequence is encoded redundantly in multiple oligonucleotides.

Figure 3A:
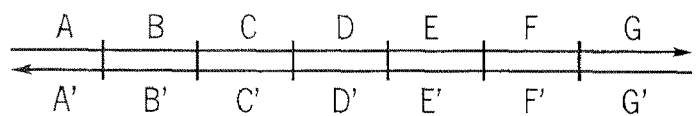
FIGS. 3A-D show an aspect of the invention for generating long DNA sequences starting from a set of many redundantly overlapped oligonucleotides, where the majority of the oligonucleotide sequence is used to generate the complementary overlap, thereby improving the possibility of annealing.

FIG. 3A. The desired target sequence, divided into segments labeled A, B, C, and so forth.

Figure 3B:
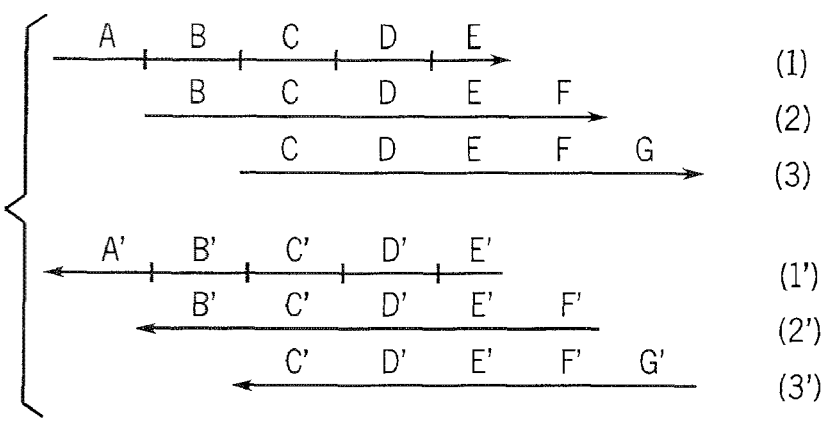

FIG. 3B. Both top and bottom strands of the target sequence are represented redundantly by multiple oligonucleotides (1, 2, 3, etc for the top strand, and 1', 2', 3' etc for the bottom).

Figure 3C:
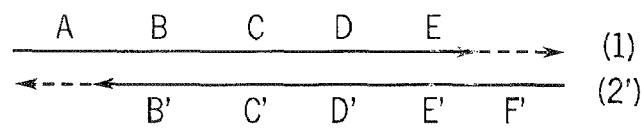

FIG. 3C. Under the most stringent annealing conditions (such as high temperature), only the oligonucleotides with a high degree of complementarity will anneal (such as 1 and 2'), giving rise to DNA duplexes which can be extended from their 3' ends.

Figure 3D:
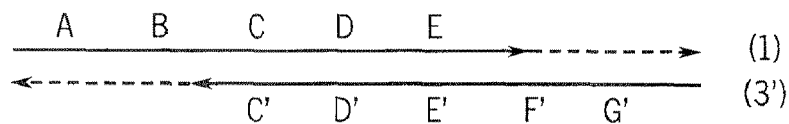

FIG. 3D. If the synthesis of a particular oligonucleotide fails (such as 2') the overall gene synthesis need not fail, since under only slightly less stringent conditions the next oligonucleotide in the set also contains the necessary sequence to anneal (such as 1 and 3'). This possibility can be seamlessly introduced into the annealing protocol by gradually reducing the temperature used. Thus the most specific interactions dominate (longest overlaps, highest melting temperatures), but interactions that are only slightly less specific (like the 1-3' annealing) will also be allowed. In the case of PCR, this progressive lowering of annealing temperature, known to those having ordinary skill in the art as "touchdown PCR", is distinct in this invention in its application to redundantly overlapped sets of oligonucleotides.

Figure 4:
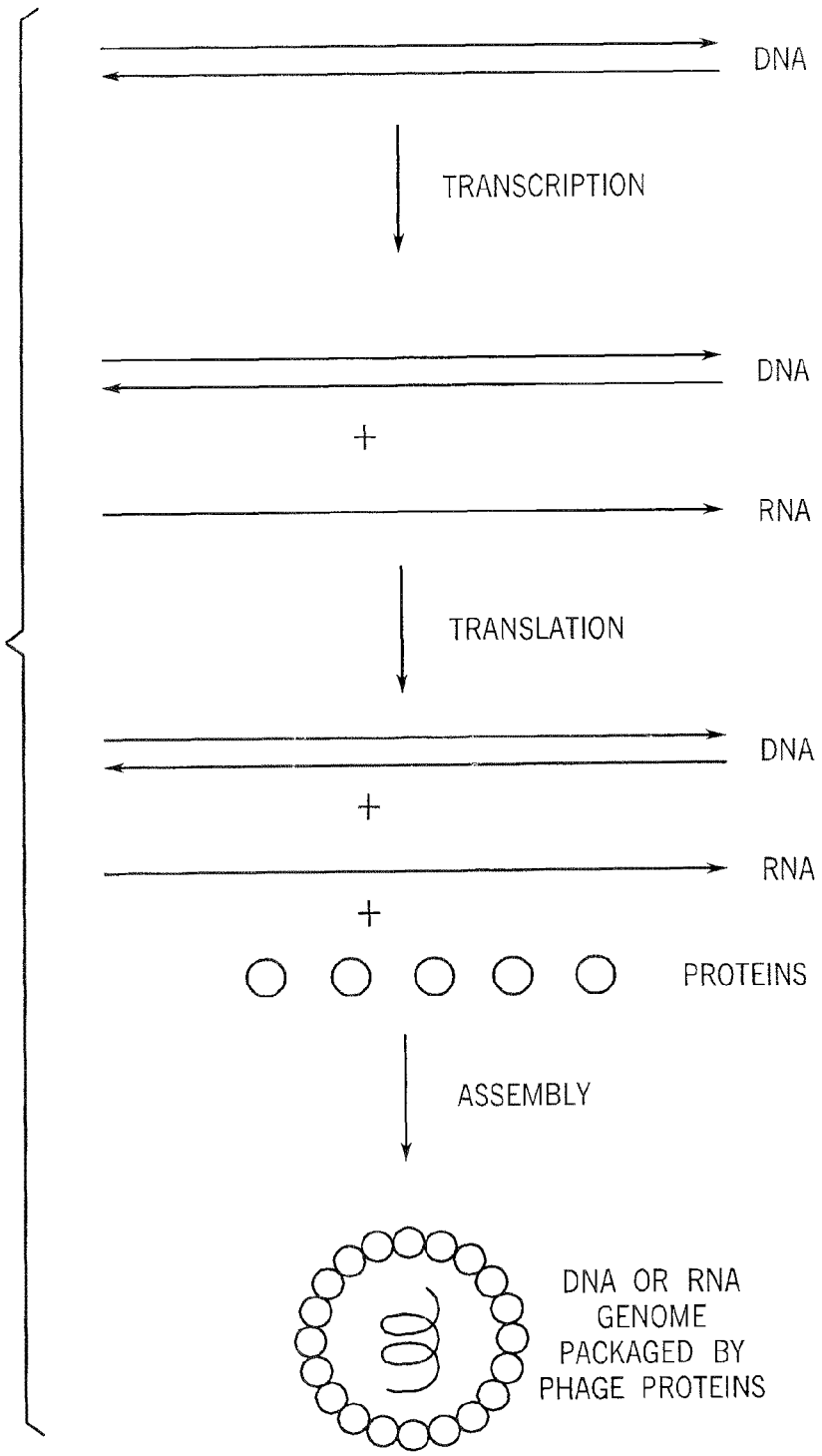
FIG. 4 shows an aspect of the invention where the desired DNA sequence encodes components needed for its own replication.

FIG. 4 illustrates the special case when the desired DNA sequence encodes components needed for its own replication. If the goal of the DNA production is not to generate a particular exact DNA sequence, but rather to produce a function (or a set of functions), then that function can be used to screen the pool of DNA molecules for the successful products. For example, the desired product can be a phage, such as a bacteriophage, that is capable of replicating in its host. The methods previously discussed could then be used to generate a long DNA molecule containing the phage genome. This DNA molecule could be used to produce phage particles using in vitro transcription and/or in vitro translation. Alternatively, the DNA could be transfected directly into the host, or treated with a packaging extract to form virus/phage particles. Regardless, only DNA molecules containing the proper components for the phage life cycle will survive this selection process, and produce viable phage. But the sequence selected for can be the genome of an entire organism, such as a bacterium. The functional screen would then be whether the organism is capable of producing a functional metabolism capable of growth, leading to DNA replication and eventually cell division.

FIG. 4. The desired sequence (such as for a phage) has been produced by the aforementioned methods, or by conventional gene synthesis techniques. Regardless of the method, many of the sequences may contain errors. In vitro transcription is employed to produce an RNA transcript of the phage DNA. Alternatively, the DNA can be transfected into a host which performs the transcription. In vitro translation of the RNA has been performed to produce proteins needed for the phage life cycle, such as packaging of the phage genome (DNA or RNA, depending on the particular phage). Alternatively, translation can also occur within a suitable host. The phage genome (DNA or RNA) is packaged by the phage proteins, producing phage particles. The phage particles which contain functional packaging proteins can infect host cells, and those containing a viable copy of the phage genome can go on to produce infectious particles within the host.

An aspect of the invention is that such DNA products are also intrinsically more error-tolerant. The DNA produced may contain deviations from the user-specified sequence. But if these deviations result in silent or tolerable mutations to the coding regions, or inconsequential changes outside the coding regions, then they are immaterial to the success of the final product. On the other hand, errors which impair the ability of the phage to replicate do not result in viable phage particles, and are therefore not observed in the final product.

When assembling especially long nucleic acid sequences, processes such as PCR will eventually become ineffective. For example, a typical length of time recommended for polymerase-based extension in a cycle of PCR is 1 minute per kb of DNA synthesized. For a 1-10 kb sequence this is a practical parameter, but for 100 kb it becomes cumbersome, and 1000 kb of linear sequence would require over 16 hours for a single cycle. Known polymerases are not sufficiently processive to accomplish this. And, since many PCR cycles are also typically employed, the total time involved to assemble and/or amplify DNA sequences on this scale becomes a great challenge.

Figure 5:
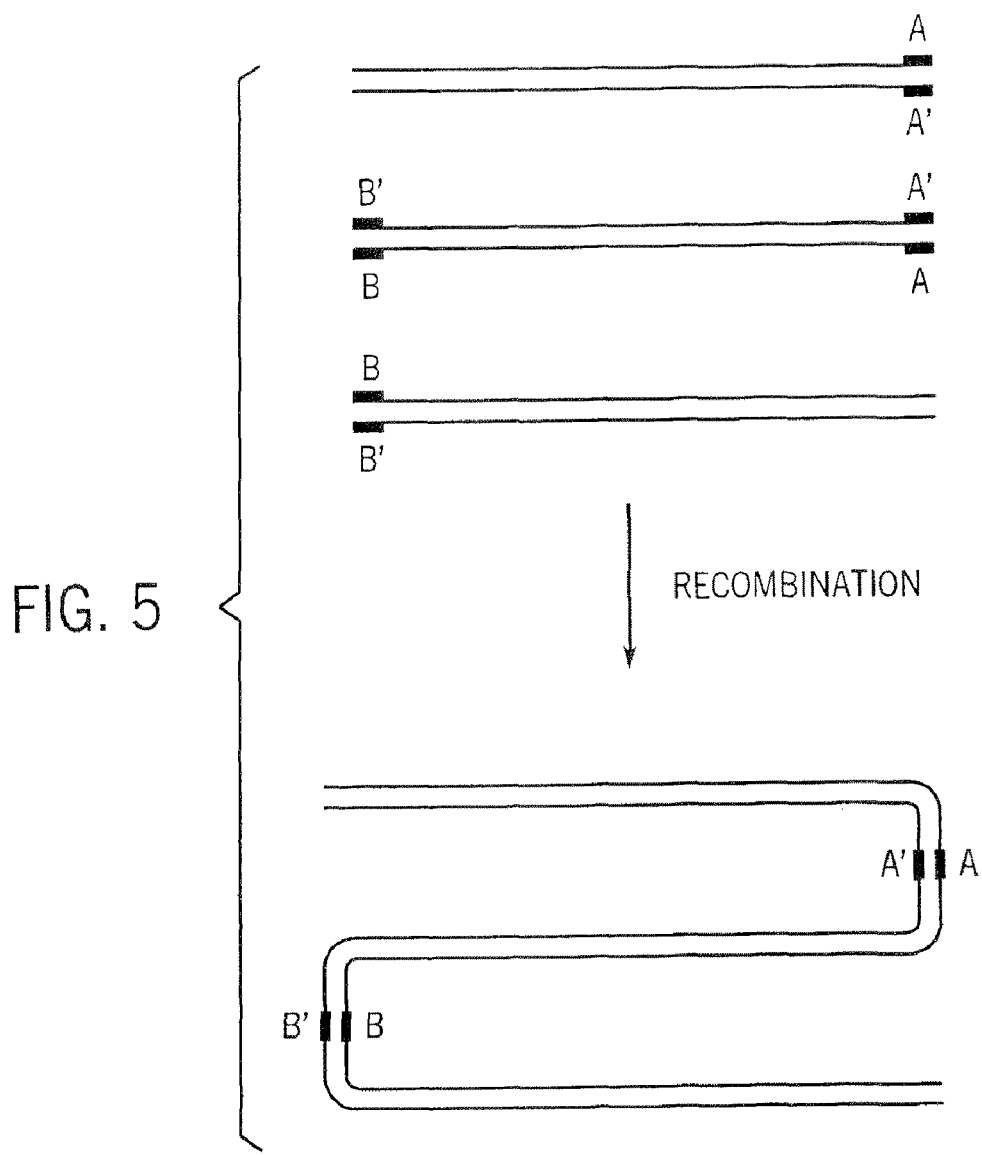
FIG. 5 shows an aspect of the invention for assembling long nucleotide sequences containing sites specifically designed to facilitate joining of separate molecules. These sequences can be sites for specific endonuclease restriction and subsequent ligation, homologous recombination, site-specific recombination, or transposition.

FIG. 5 shows a method for assembling long DNA sequences. Each sequence contains one or more regions containing sites specifically designed to facilitate joining of the separate molecules. These sequences can be sites for specific endonuclease restriction and subsequent ligation, homologous recombination, site-specific recombination (such as used by some viral integrases), or transposition. The joining sites need not be at the ends of linear DNA. In fact, the starting and final molecules can be linear DNA, circular DNA, or some combination. FIG. 5 illustrates the homologous recombination of linear DNA duplexes. These processes can be performed in vitro, though there will be advantages to performing them in living organisms as well, such as the use of host factors to facilitate the process of joining, as well as the use of host replication machinery to ensure the most efficient and accurate amplification of the exogenous DNA. Such joining mechanisms are found in nature and are well known to those having ordinary skill in the art for combining DNA molecules of various sizes. For example, an organism such as *Deinococcus radiodurans* is able to reassemble its entire genome even after it has been sheared into many separate pieces. A novel aspect of this invention is the application of these procedures to generate large DNA molecules whose entire sequences are completely determined by the user de novo (as opposed to simply being derived from an organism, such as by conventional cloning).

FIG. 5. Three long DNA sequences, with end regions specifically designed for homologous recombination. The A and A' ends of the top two DNA duplexes undergo homologous recombination, joining these into a longer duplex. The same type of joining occurs between the bottom two duplexes, using a different set of homologous sequences, B and B'.

This disclosure also details methods for an 'all-biological linear synthesis' of nucleic acids. This synthetic strategy employs the use of biological molecules as protecting groups, and all nucleotide addition and deprotection steps are performed using biological enzymes. Such a synthetic technique will ultimately yield nucleotides that are longer and have higher fidelity (i.e. have less errors) than those synthesized by standard techniques. The synthesis is performed in biological conditions (aqueous environment at neutral pH), thereby eliminating the damage to the nucleotides during the process. Since the synthesis proceeds in the 5'-3' direction, biological enzymes can be used for subtractive error-correction at the 3' terminus—an option not available in standard solid-phase synthetic schemes. For methods and materials known in the art related to protecting groups, see e.g., Muller, C., Even, P., Viriot, M., Carre, M., *Protection and Labelling of Thymidine by a Fluorescent Photolabile Group*, HELVETICA CHIMICA ACTA, 84, 3735-3741 (2001) and Fedoryak, O. D., Dore, T. M., *Brominated Hydroxyquinoline as a Photolabile Protecting Group with Sensitivity to Multiphoton Excitation*, ORGANIC LETTERS, Vol. 4, No. 20, 3419-3244 (2002) all of which are hereby incorporated by reference.

An all-biological synthetic strategy is particularly attractive when coupled with the single-molecule feedback and error-correcting schemes in this disclosure. These schemes typically utilize electrophoretic force measurements, based on the intrinsic negative-charge of the DNA phosphate backbone, as the feedback mechanism during nucleotide addition steps. Oligonucleotides generated by an all-biological synthetic scheme are always negatively charged at each step in the cycle. Thus, this process provides a negatively charged backbone compared to the standard (phosphoramidite) approach, where the backbone is neutral until the oligonucleotide has reached its full-desired length.

Figure 6A:
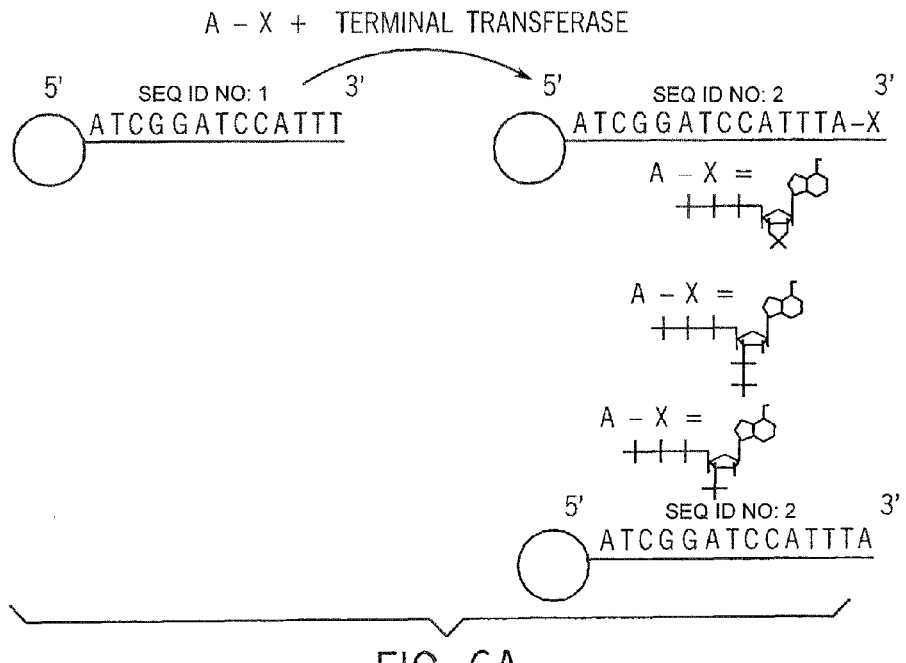
FIGS. 6A and 6B show an embodiment of the invention employing an all-biological synthetic strategy for the synthesis of both single-stranded and double-stranded DNA using nucleotides with various 3'-phosphate protecting groups, such as but not limited to, peptide, carbohydrate, diphosphate, or phosphate derivative 3'-phosphate protecting groups.

FIG. 6A. Synthesis of single-stranded DNA with a peptide or carbohydrate 3'-phosphate protecting group. After an addition to the nascent DNA strand (SEQ ID NO.:1) by a capped nucleotide or oligonucleotide, a protease cleaves the bond between the capping group and the most recently added nucleotide, forming an oligonucleotide (SEQ ID NO.: 2) comprising one more nucleotide base than the nascent DNA strand. The monomer addition can be done with traditional chemical synthesis or enzymatically (by using a terminal transferase or nucleotide ligase). DNA polymerase or nucleotide ligase can be used to add a 3' capped nucleotide or oligonucleotide to the 3' end of the nascent strand. DNA ligase can also be used to add a 5' capped nucleotide or oligonucleotide to the 5' end of the nascent strand. A sample method comprises the use of a tyrosine residue bound to the 3' hydroxyl of the newly added monomer as a capping group. Tyrosyl-DNA phosphodiesterase is used to eliminate the capping group and continue addition of new monomers. Aminoacyl hydrolase, Proteinase K or an evolved enzyme can be used to eliminate other peptide capping groups.

Figure 6B:
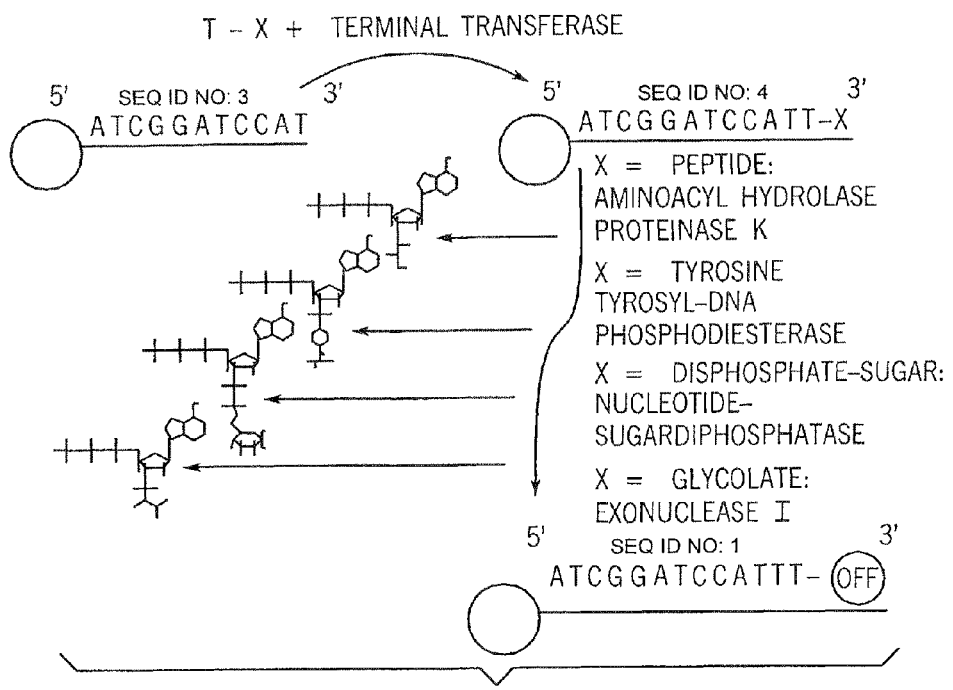

FIG. 6B. Synthesis of single-stranded DNA with diphosphate or phosphate derivative as a 3'-phosphate protecting group. After an addition to the nascent DNA strand (SEQ ID NO.:3) by a capped nucleotide or oligonucleotide, forming an oligonucleotide (SEQ ID NO.: 4) comprising one more nucleotide base than the nascent DNA strand, a phosphatase cleaves the bond between the capping group and the most recently added nucleotide. The monomer addition can be done with traditional chemical synthesis or enzymatically (by using a terminal transferase or nucleotide ligase). DNA polymerase or nucleotide ligase can be used to add a 3' capped nucleotide or oligonucleotide to the 3' end of the nascent strand. DNA ligase can also be used to add a 5' capped nucleotide or oligonucleotide to the 5' end of the nascent strand. The capping group is a single phosphate at the 3' or 5' end of the monomer (depending on the chemistry), a 2'3' cyclic phosphate, or multiple beaded phosphate groups, or other phosphate derivatives. A deoxynucleotide 3' phosphatase, cleaves phosphates from the 3' end of the nascent strand after a nucleotide or oligonucleotide addition has occurred, leaving a free 3' hydroxyl. In the cyclic phosphate case, 2'3' cyclic nucleotide 2' phosphodiesterase and deoxynucleotide 3' phosphatase together cleave the cyclic phosphate and free a 3' hydroxyl.

Figure 7:
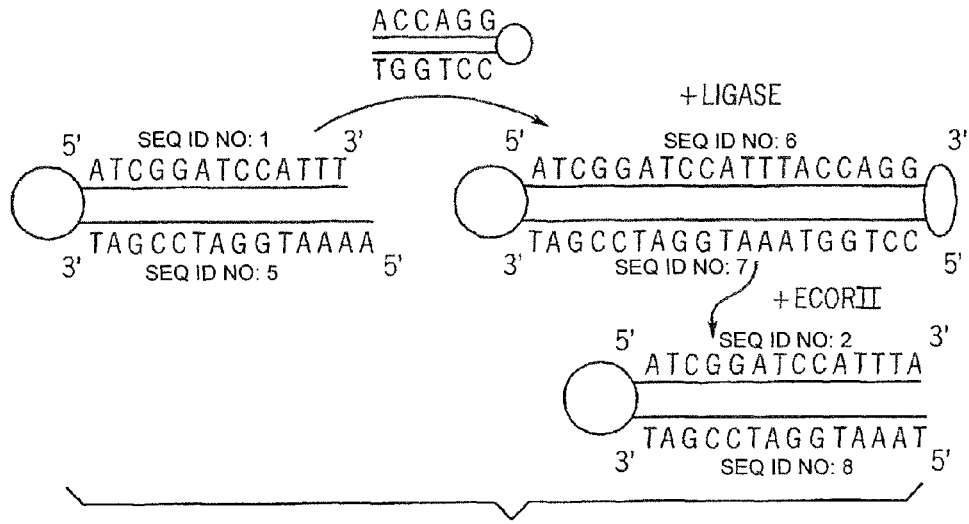
FIG. 7 shows an embodiment of the invention employing an all-biological synthetic strategy for the synthesis of double-stranded DNA using an oligonucleotide capping group.

FIG. 7. Synthesis of a double-stranded DNA with an oligonucleotide capping group. The capping group is comprised of a nucleotide or short oligonucleotide that can be cleaved by a restriction enzyme from the nascent double stranded DNA (SEQ ID NO.:1; SEQ ID NO.:5). The oligonucleotide cap may or may not form a DNA secondary structure such as a hairpin loop. After the addition of a capped nucleotide or oligonucleotide, which forms a double-stranded oligonucleotide (SEQ ID NO.:6, SEQ ID NO.:7) comprising additional nucleotide bases as compared to the nascent double-stranded DNA, a restriction enzyme which recognizes the capping nucleotide sequence will cleave the fragment 3' to the newly added nucleotide, resulting in a double-stranded oligonucleotide (SEQ ID NO.: 2, SEQ ID NO.: 8) comprising an additional nucleotide base pair as compared to the nascent double-stranded DNA. A dsDNA oligonucletide with the desired nucleotide or oligonucleotide to be added would also contain a restriction site 3' to the leading strand, whose 3' end of the leading strand would possess a 2'3' dideoxy nucleotide (or other capping group such that prevents multiple monomer addition) and the lagging strand a 5' deoxy ribose (or other capping group that prevents multiple monomer addition). For this particular scheme a Type III or other restriction endonuclease would be used to cut outside of the recognition site, thus leaving only the nascent strand with the newly added nucleotide or oligonucleotide. Thereby, the sequence of the monomer is X—R where X is a specific nucleotide or oligonucleotide sequence that will be added to the nascent strand by nucleotide ligase and R is the restriction enzyme recognition site which will be cleaved after ligation of the new monomer. The desired nucleotide (X) will remain on the nascent strand. This procedure is repeated to create a specific oligonucleotide sequence. Different restriction enzymes and corresponding capping nucleotides or sequence redesign may be required for the creation of desired oligonucleotides in order to prevent sequence recognition in the nascent strand. DNA ligase or topoisomerase may be covalently bound to the end or beginning of the monomer to facilitate monomer addition.

Figure 8A:
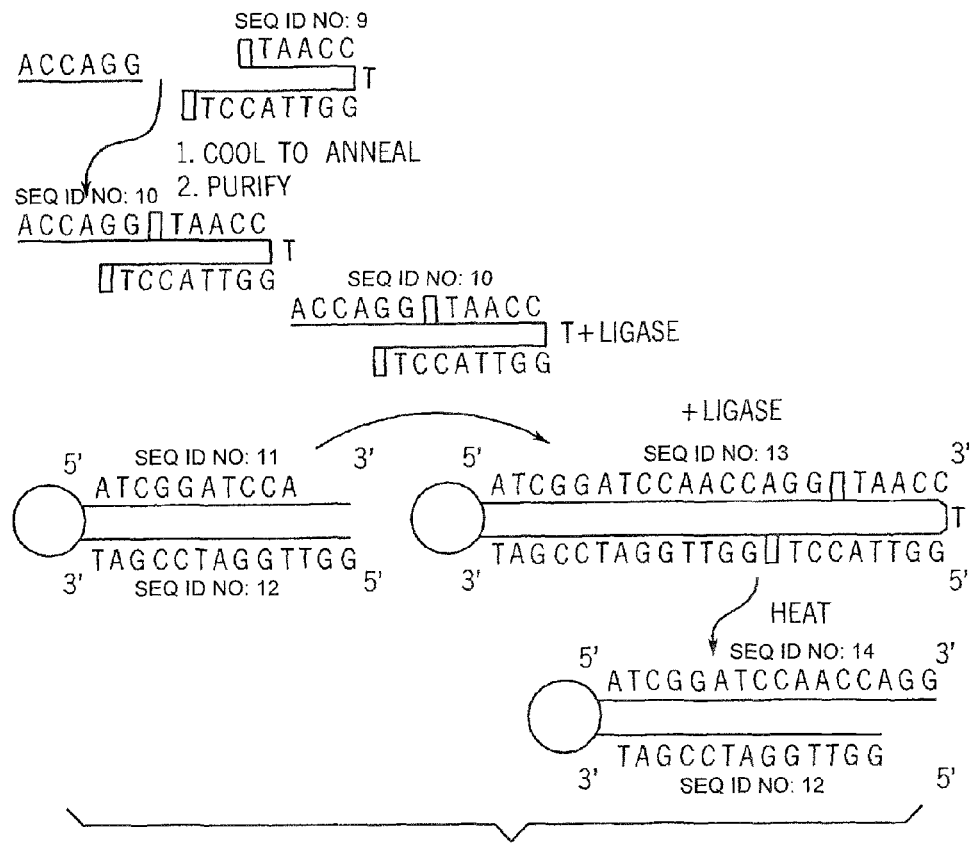
Figure 8B:
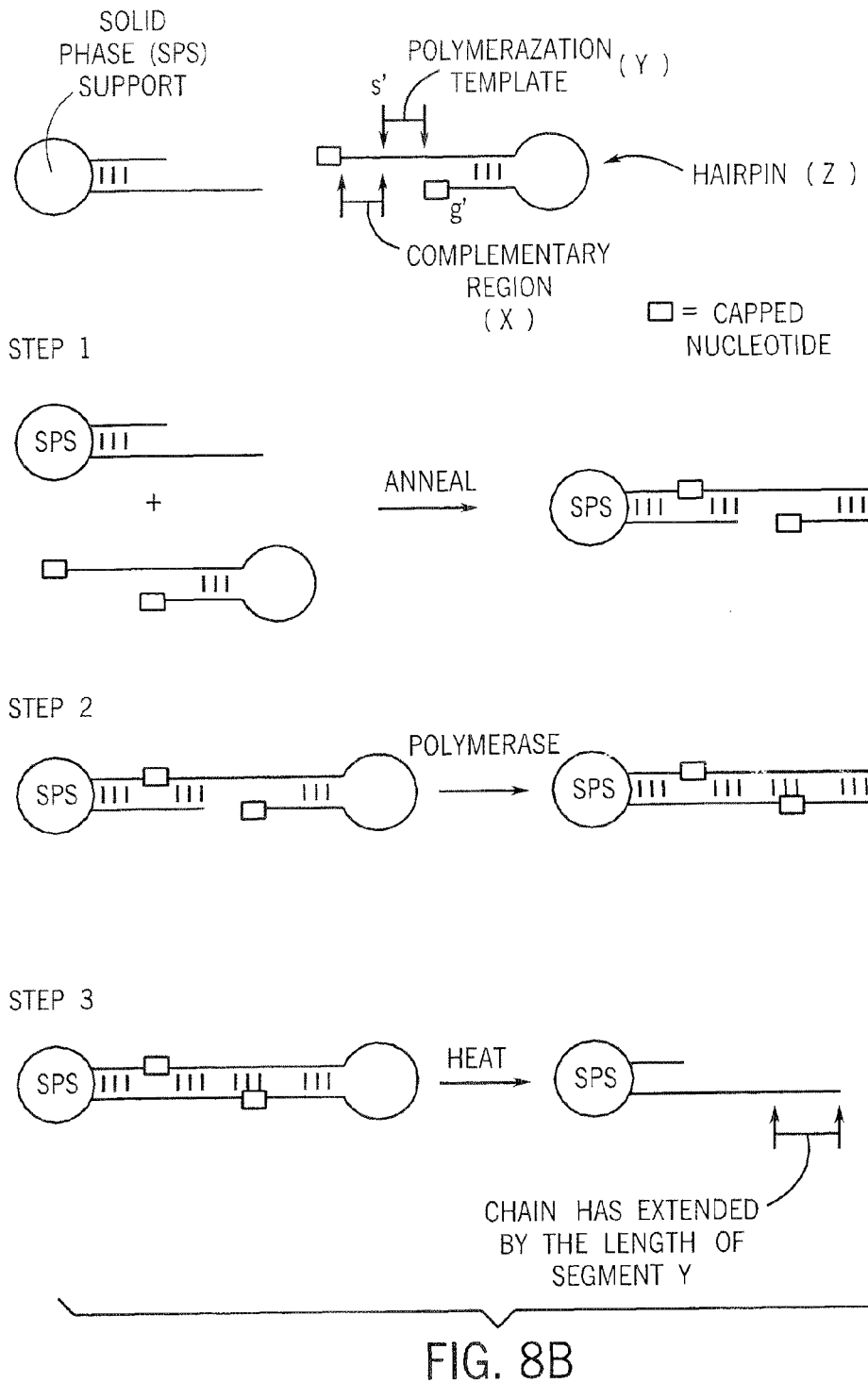

FIGS. 8A-C. Synthesis of double-stranded DNA using oligonucleotide hairpin-loops as heat-removable protecting groups. Oligonucleotides with secondary conformational structures, such as DNA hairpin-loops (also termed stemloops, and molecular beacons), can also be used as protecting groups. A similar approach has been reported where hairpin-loops are enzymatically removed by restriction enzymes, a process termed "synthetic cloning" or "splinking" The methods described in FIGS. 8A-C differ from previously reported methods in the general structure of the hairpin-loops, and because the removal method is gentle heating. Furthermore, gentle heating is potentially an improved method of deprotection over enzymatic removal because 1) heat distributes more quickly and uniformly than enzymes because the enzymatic removal rate is diffusion-limited, and 2) gentle heating is a lower-cost resource than restriction enzymes.

FIG. 8A. In this scheme for double-stranded DNA synthesis, the monomer unit that is added to the growing nascent strand is a complex comprised of DNA hairpin-loop (SEQ ID NO.: 9) and an annealed short oligonucleotide insert segment. Addition monomers are first produced by annealing a hairpin-loop and a partially complementary short oligonucleotide insert segment. At one end, the insert segment sequence has at least one base which is complementary to the last base added to the nascent strand, and at the other end of the insert sequence there is at least 1 base which is complementary to its respective hairpin capping group. Both the 5' and 3' ends of the hairpin structure lack reactive hydroxyl groups so are unable to ligate to the insert strand or nascent strand. After hairpins and inserts are annealed, they are purified such that only single hairpin-insert monomers (SEQ ID NO.: 10) are present. The hairpin-insert monomers are added to the nascent double strand (SEQ ID NO.: 11, SEQ ID NO.: 12) and DNA ligase is used to ligate the insert segment to the nascent strand, forming a double-stranded oligonucleotide with a hairpin (SEQ ID NO.: 13) that comprises additional bases as compared to the nascent double-stranded DNA. The capping group is removed by varying the pH or temperature of the solution and further monomers added to create a specific double stranded oligonucleotide sequence (SEQ ID NO.: 14, SEQ ID NO.: 12).

FIG. 8B. Synthesis of single-stranded DNA by PCR using a DNA hairpin-loop as both the PCR primer and the protecting group. The hairpin-loop monomer contains three regions: 1) a partially complementary oligonucleotide sequence at the 5' end that serves as the PCR primer (X), 2) an oligonucleotide sequence that serves as the template for the polymerization (Y), and 3) terminal hairpin-loop that serves as the protecting group (Z). First, the partially complementary region of the hairpin-loop (X) anneals to the nascent strand. Second, polymerase proceeds to copy the template region of the hairpin-loop (Y). The hairpin-loop monomer is capped at both the 5' and 3' ends, and therefore, is incapable of being incorporated into the growing nascent strand during the polymerization step. The polymerization reaction terminates at the 3'-end of the hairpin-loop monomer because it is protected. The hairpin-loop is removed by gentle heating. Because the 5'-end of the hairpin-loop is capped, the addition to the growing oligonucleotide is single-stranded.

FIG. 8C. Synthesis of double-stranded DNA by PCR using a DNA hairpin-loop as both the PCR primer and the protecting group. The synthetic approached presented in FIG. 8B can also be used to synthesize double-stranded DNA. Prior to removing the hairpin-loop by heating in the scheme described in FIG. 8B, a short oligonucleotide (W) is introduced that is complementary to the growing single-strand (bottom strand in the figure). The oligonucleotide (W) is added to the top strand of the growing chain by polymerase or ligase. After this addition step, the hairpin-loop is removed by gentle heating. When synthesizing very long DNA, the double-stranded synthesis approach shown in FIG. 8C is preferred over the single-strand approach shown in FIG. 8B because of the increased probability that the hairpin-loop anneals to the terminus of the growing strand.

Part II. DNA Error Control

In the process of constructing long molecules of nucleic acid, one needs to confront the potential errors that are expected to arise in those molecules. As the molecule length grows, conventional methods of error-reduction, such as denaturing high performance liquid chromatography (DH-PLC), become prohibitively cumbersome, time-consuming, and costly. Feedback and quality control in standard batch synthesis procedures are often employed, such as spectroscopic and potentiometric monitoring of the removal of 5'-protecting groups, and iterative DHPLC purification. However, spectroscopic and potentiometric monitoring do not provide information on individual oligonucleotides strands being synthesized, and quality control by purification does not provide 100% sequence fidelity. A novel aspect of this invention presents a method for dramatically reducing errors in synthesized molecules of nucleic acid.

Biological organisms have means to detect errors in their own DNA sequences, as well as repair them. One component of such a system is a mismatch binding protein which can detect short regions of DNA containing a mismatch, a region where the two DNA strands are not perfectly complementary to each other. Mismatches can be the result of a point mutation, deletion, insertion, or chemical modification. For the purpose of this invention, a mismatch includes base pairs of opposing strands with sequence A-A, C-C, T-T, G-G, A-C, A-G, T-C, T-G, or the reverse of these pairs (which are equivalent, i.e. A-G is equivalent to G-A), a deletion, insertion, or other modification to one or more of the bases. The mismatch binding proteins (MMBPs) have previously been used commercially for the detection of mutations and genetic differences within a population (SNP genotyping), but prior to this disclosure, have not been used for the purpose of error control in designed sequences. Many representative proteins exist capable of mediating activities of mismatch recognition, endonuclease activity, and recombination activity. For example, recombination activity may be accomplished using some subset of the phage Lambda proteins Exo, Gam, Beta, or their functional homologs. For example, mismatch recognition may be performed by MutS or one of its functional homologs. For methods and materials know in the art relating to mismatch recognition, endonuclease activity, and recombination activity, see e.g., Yang, B., Wen, X., Kodali, S., Oleykowski, C. A., Miller, C. G., Kulinski, J., Besack, D., Yeung, J. A., Kowalski, D., Yeung, A. T., *Purification, Cloning, and Characterization of the CEL I Nuclease*, BIOCHEMISTRY, 39, 3533-3541 (1999); Youil, R., Kemper, B., Cotton, R. G. H., *Detection of 81 of 81 Known Mouse β-Globin Promoter Mutations with T4 Endonuclease VII—The EMC Method*, GENOMICS, 32, 431-435 (1995); Jackson, B. A., Barton, J. K., *Recognition of DNA Base Mismatches by a Rhodium Intercalator*, J. AM. CHEM. SOC., 119, 12986-87 (1997); Nakatani, K., Sando, S., Saito, I., According to the invention, mismatch recognition can be used to control the errors generated during oligonucleotide synthesis, gene assembly, and the construction of nucleic acids of different sizes. (Though biological systems use this function when synthesizing DNA, it requires the presence of a template strand. For de novo synthesis, employed for this invention, one is starting by definition without a template.) Mismatch recognition can be accomplished by the action of a protein (such as bacterial MutS proteins, eukaryotic MSH proteins, T4 endonuclease VII, T7 endonuclease I, and celery CelI) a small molecule (for example dimeric 2-amino-1,8-naphthyridine), or a process (such as temperature gradient gel electrophoresis or denaturing HPLC). In a preferred embodiment of the invention, recognition is accomplished employing a mismatch recognition protein such as MutS or its functional homologs.

When attempting to produce a desired DNA molecule, a mixture typically results containing some correct copies of the sequence, and some containing one or more errors. But if the synthetic oligonucleotides are annealed to their complementary strands of DNA (also synthesized), then a single error at that sequence position on one strand will give rise to a base mismatch, causing a distortion in the DNA duplex. These distortions can be recognized by a mismatch binding protein. (One example of such a protein is MutS from the bacterium *Escherichia coli*.) Once an error is recognized, a variety of possibilities exist for how to prevent the presence of that error in the final desired DNA sequence.

When using pairs of complementary DNA strands for error recognition, each strand in the pair may contain errors at some frequency, but when the strands are annealed together, the chance of errors occurring at a correlated location on both strands is very small, with an even smaller chance that such a correlation will produce a correctly matched Watson-Crick base pair (e.g. A-T, G-C). For example, in a pool of 50-mer oligonucleotides, with a per-base error rate of 1%, roughly 60% of the pool ($0.99^{50}$) will have the correct sequence, and the remaining forty percent will have one or more errors (primarily one error per oligonucleotide) in random positions. The same would be true for a pool composed of the complementary 50-mer. After annealing the two pools, approximately 36% ($0.6^2$) of the DNA duplexes will have correct sequence on both strands, 48% (2×0.4×0.6) will have an error on one strand, and 16% ($0.4^2$) will have errors in both strands. Of this latter category, the chance of the errors being in the same location is only 2% (1/50) and the chance of these errors forming a Watson-Crick base pair is even less (1/3×1/50). These correlated mismatches, which would go undetected, then comprise 0.11% of the total pool of DNA duplexes (16×1/3×1/50). Removal of all detectable mismatch-containing sequences would thus enrich the pool for error-free sequences (i.e. reduce the proportion of error-containing sequences) by a factor of roughly 200 (0.6/0.4 originally for the single strands vs. 0.36/0.0011 after mismatch detection and removal). Furthermore, the remaining oligonucleotides can then be dissociated and re-annealed, allowing the error-containing strands to partner with different complementary strands in the pool, producing different mismatch duplexes. These can also be detected and removed as above, allowing for further enrichment for the error-free duplexes. Multiple cycles of this process can in principle reduce errors to undetectable levels. Since each cycle of error control may also remove some of the error-free sequences (while still proportionately enriching the pool for error-free sequences), alternating cycles of error control and DNA amplification can be employed to maintain a large pool of molecules.

According to the invention, if the DNA duplexes in question have been amplified by a technique such as the polymerase chain reaction (PCR) the synthesis of new (perfectly) complementary strands would mean that these errors are not immediately detectable as DNA mismatches. However, melting these duplexes and allowing the strands to re-associate with new (and random) complementary partners would generate duplexes in which most errors would be apparent as mismatches, as described above.

Many of the methods described below can be used together, applying error-reducing steps at multiple points along the way to producing a long nucleic acid molecule. Error reduction can be applied to the first oligonucleotide duplexes generated, then, for example, to intermediate oligonucleotides of about 500-mers to about 1000-mers, and then even to larger full length nucleic acid sequences of about 10,000-mers or more.

This invention provides methods for dramatically reducing errors in large-scale gene synthesis. It is possible to generate the nucleic acid of interest by direct linear synthesis, but on a length scale previously made impossible by the error rates associated with chemical synthesis of oligonucleotides. For the purpose of this invention, direct observation of products at the single-molecule level during the synthesis process provides a means to monitor and even correct errors that occur during synthesis. Since DNA can be amplified by PCR, large amounts of oligonucleotides can be copied from perfect oligonucleotide with the fidelity of polymerase activity (one error in $10^3$-$10^8$).

There are several observation methods for single-molecule techniques, such as single-molecule fluorescence spectroscopy, nanopore analysis, and force microscopy using atomic force microscopes, optical tweezers, and magnetic tweezers. Direct observation of single-molecules enables feedback during the synthesis of an individual oligonucleotide. Therefore, the time per addition (nucleotide or short oligonucleotide) is minimized, whereas typical addition times are in excess in order to maximize the yield per step. Furthermore, feedback at the single-molecule level also enables error-correction, thereby greatly increasing the fidelity of the oligonucleotide.

The methods described herein can employ various optical tweezers and magnetic tweezers, electrophoretic techniques, and microscopy techniques. Designs of optical and magnetic tweezers include, but are not limited to: 1) single-beam optical tweezers that trap one particle, 2) single-beam optical tweezers that trap multiple particles, 3) parallel multiple-beam optical tweezers, 4) optical tweezers with single-molecule fluorescence detection capability, 5) single-pole, double-pole, quadrupole, sextapole, octapole magnetic tweezers using electromagnetic coils, 6) single-pole and double-pole tweezers using permanent magnets, 7) parallel multiple-pole magnetic tweezers, and 8) magneto-optical tweezers. Single-molecule electrophoretic techniques include, but are not limited to: 1) electrophoresis in a static electric field, 2) electrophoresis in a variable electric field, and 3) capillary gel electrophoresis. For methods and materials known in the art related to electrophoresis, see e.g., Wu, X., Kasashima, T., *An Improvement of the On-Line Electrophoretic Concentration Method for Capillary Electrophoresis of Proteins and Experimental Factors Affecting the Concentration Effect*, ANALYTICAL SCIENCES, 16, 329-331 (2000), which is hereby incorporated by reference. Single-molecule microscopy techniques include, but are not limited to: 1) fluorescence with single-photon excitation, 2) fluorescence with multi-photon excitation, 3) differential phase contrast microscopy, and 4) differential interference contrast microscopy. These examples are to be considered in all respects illustrative rather than limiting on the invention described herein. For methods and materials known in the art related to various magnetic, optical, magneto-optical, electromagnetic, dipole, and quadrupole traps, see e.g., Goose, C., Croquette, *Magnetic Tweezers: Micromanipulation and Force Measurement at the Molecular Level*, BIOPHYS. J., 82, 3314-29 (2002); Ballerini, R., Capitanio, M., De Pas, M., Giuntini, M., *Three-Dimensional Magneto-Optic Trap for Micro-Object Manipulation*, OPTICS LETTERS, Vol. 26, No. 17, 1359 (2001); Wirtz, D., *Direct Measurement of the Transport Properties of a Single DNA Molecule*, PHYSICAL REVIEW LETTERS, Vol. 75, No. 12, 2436 (1995); Tanase, M., Hultgren, A., Searson, P. C., Meyer, G. J., Reich, D. H., *Magnetic Trapping of Multicomponent Nanowires*, (2001); Amblard, F., Yurke, B., Pargellis, A., Leibler, S., *A Magnetic Manipulator for Studying Local Rheology and Micromechanical Properties of Biological Systems*, REV. SCI. INSTRUM., Vol. 67, No. 3, 819 (1996); Lee, C. S., Lee, H., Westervelt, R. M., *Microelectromagnets for the Control of Magnetic Nanoparticles*, APPL. PHYS. LETT., Vol. 79, No. 20, 3308 (2001); Garbow, N., Evers, M., Palberg, T., *Optical Tweezing Electrophoresis of Isolated, Highly Charged Colloidal Spheres*, COLLOIDS AND SURFACES A: PHYSIOCHEM. ENG. ASPECTS, 195, 227-241 (2001); Lang, M. J., Asbury, C. L., Shaevitz, J. W., Block, S. M., *An Automated Two-Dimensional Optical Force Clamp for Single Molecule Studies*, BIOPHYS. J., 83, 491-501 (2002); Galneder, R., Kahl, V., Arbuzova, A., Rebecchi, M., Radler, J. O., McLaughlin, S., *Microelectrophoresis of a Bilayer-Coated Silica Bead in an Optical Trap: Application to Enzymology*, BIOPHYS. J., 80, 22988-2309 (2001); Assi, F., Jenks, R., Yang, J., Love, C., Prentiss, M., *Massively Parallel Adhesion and Reactivity Measurements Using Simple and Inexpensive Magnetic Tweezers*, J. APPL. PHYS., Vol. 92, No. 9, 5584 (2002); Voldman, J., Braff, R A., Toner, M., Gray, M. L., Schmidt, M. A., *Holding Forces of Single-Particle Dielectrophoretic Traps*, BIOPHYS. J., 80, 531-541 (2001); Huang, H., Dong, H., Sutin, J. D., Kamm, R. D., So, P. T. C., *Three-Dimensional Cellular Deformation Analysis with a Two-Photon Magnetic Manipulator Workstation*, BIOPHYS. J., 82, 2211-2223 (2002), Haber, C., Wirtz, D., *Magnetic Tweezers for DNA Micromanipulation*, REV. SCI. INSTRUM., Vol. 71, No. 2, 4561 (2000); Hosu, B. G., Jakab, K., Banki, P., Toth, F. I., Forgacs, G., *Magnetic Tweezers for Intracellular Applications*, REV. SCI. INSTRUM., Vol. 74, No. 9, 4158 (2003); Smith, S. B., Finzi, L., Bustamante, C., *Direct Mechanical Measurements of the Elasticity of Single DNA Molecules by Using Magnetic Beads*, SCIENCE, Vol. 258, No. 5085, 1122-1126 (1992); all of which are hereby incorporated by reference.

The methods described herein employ various synthetic strategies. These strategies include, but are not limited to: 1) phosphoramidite, phosphodiester, and phosphotriester chemistries, 2) PCR and LCR assembly schemes, and 3) all biological synthesis schemes using biological protecting groups. These examples are to be considered in all respects illustrative rather than limiting on the invention described herein.

The methods described herein require a solid-phase support to be functionalized with only one oligonucleotide in order to have single-molecule feedback and error-correction capabilities. In the preferred embodiment, this monofunctionalization of the solid-phase support is performed based on the methods reported by U.S. application Ser. No. 10/621,790, titled "Nanoparticle Chains and Preparation Thereof", filed Jul. 17, 2003, now U.S. Pat. No. 7,476,442, issued Jan. 13, 2009, which is hereby incorporated by reference.

Figure 9A:
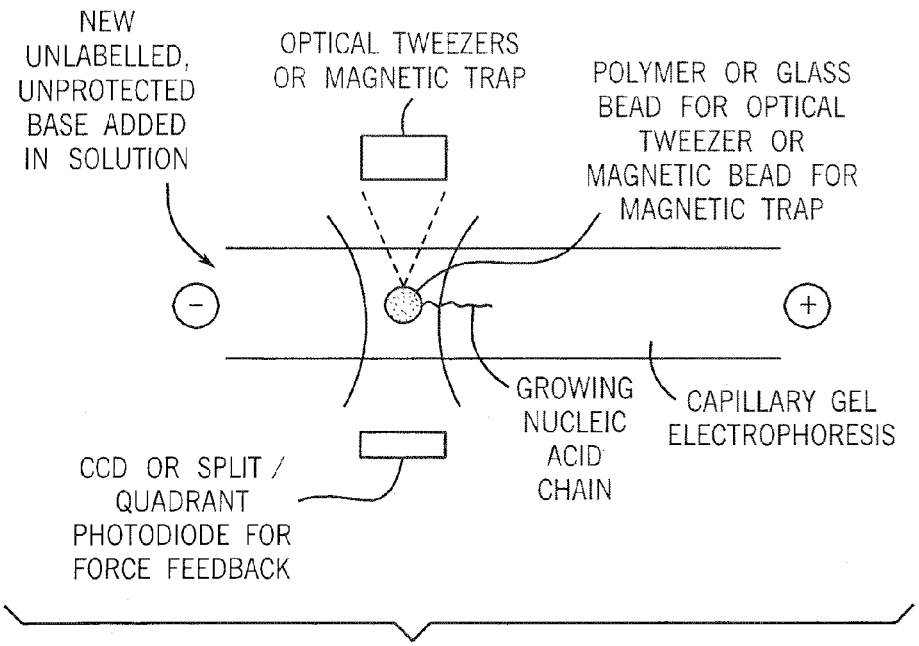
FIGS. 9A and 9B show an embodiment of the invention employing force-feedback, in this case optical tweezers and/or a magnetic trap, in order to screen for and correct errors.
Figure 9B:
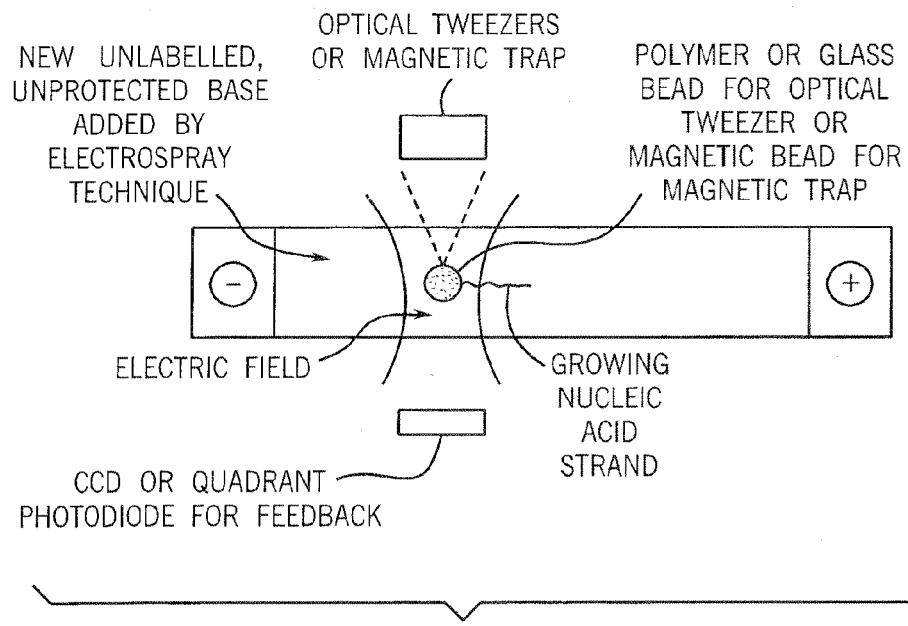

FIGS. 9A and 9B. Force-feedback using magnetic and optical tweezers.

FIG. 9A. In this scheme, the double-stranded DNA is grown off a solid-phase support by sequential overlapping short DNA strands by annealing partially complementary oligonucleotides, followed by enzymatic ligation. The solid-phase support is a superparamagnetic bead comprised of a dielectric polymer loaded with superparamagnetic nanoporticles. The support is held in a fixed equilibrium position by applying an electric field and magnetic field gradient created by the magnetic tweezers that opposes the electrophoretic force. When an oligonucleotide is annealed to the growing strand, the negatively charged phosphate backbone adds charge to the bead-strand complex. However, the added oligonucleotide adds essentially no mass or surface area to the complex. Assuming the zeta-potential of the dielectric bead is constant, the addition of an oligonucleotide strand is the only contribution to the increase in electrophoretic force felt by the particle. The increased electrophoretic force moves the bead from its equilibrium position, and the magnetic field gradient must be increased to restore the bead to its equilibrium position. Optically determined bead velocity and restoration force correspond to the number of bases added. Therefore, the length of the added strand can be ensured to be correct. Optical detection can be by way of a CCD or split-photodiode.

FIG. 9B. The scheme in FIG. 9A can also be modified and employ optical tweezers to apply an optical force rather than a magnetic force. In this particular scheme, the optical force can, but need not oppose the electrophoretic force. The schemes in FIGS. 9A and 9B can be coupled using magneto-optical tweezers. The optical and magnetic forces can be created simultaneously or independently of one another.

FIG. 10. Force-feedback systems using only electrophoresis.

DNA ligase- and kinase-mediated single molecule synthesis with feedback control. In this scheme, a single strand of DNA is synthesized on a fluorescent bead functionalized with a single phosphate group, and electrophoretically passed through a medium with excess ATP, kinase, and ligase. The rate of motion of the bead is monitored and used as the feedback mechanism. There are no protecting groups incorporated in this synthetic scheme. All synthetic steps employ enzymes. First, excess ATP is passed through the medium simultaneously (with the bead). Excess ATP will pass through the medium much faster than the bead. The kinase will catalyze the formation of a triphosphate on the bead using ATP. When this occurs, the rate of motion of the bead will change, due to a change in the charge/mass ratio. The measurement of this change thus serves to indicate a successful reaction. Once the triphosphate has formed on the bead, excess free nucleotide is passed through the medium. These small molecules will pass through the medium much faster than the bead. DNA ligase will catalyze the addition of the nucleotide, releasing a diphosphate. The rate of motion of the bead is reduced because the loss of the diphosphate decreases the charge/mass ratio. This serves as feedback for base addition. Multiple-nucleotide addition in this step should not occur because after one addition, there is no triphosphate present in the system, which DNA ligase needs to add the base. Once a successful nucleotide addition is detected, more ATP is introduced into the system and the described cycle repeats. In one embodiment of this aspect of the invention, the ligase and kinase activities can be localized in different regions of the medium, and the bead can be moved back and forth between these regions to allow tighter control over the synthetic steps.

Heat may also be used as an additional feedback and error correction mechanism in force feedback systems. For example, the force-feedback systems shown in FIGS. 9A-B and 10 can also employ heat as additional feedback and error-correction. Prior to enzymatic ligation, the melting point of the small oligonucleotide in contact with the growing nucleic acid strand will be lowered if base-pair mismatches occur. The controlled application of heat after detected annealing can provide additional feedback about base-pair mismatches. If the oligonucleotide dehybridizes from the growing strand as the melting point is approached, but not reached, a base-pair mismatch is detected when a decrease in magnetophoretic force, or increase in electrophoretic force is required to keep the bead in equilibrium. Because the erroneous strand is removed by heat, this feedback process is also an error-correction mechanism.

Nucleotide removal by exonuclease activity may also be used for error-correction in force-feedback systems. The schemes in the force-feedback systems shown in FIGS. 9A-B and 10 may also employ nucleotide removal by exonuclease activity as an error-correction mechanism. This type of error-correction is particular useful for correcting errors after enzymatic ligation of an erroneous strand. Whereas it would be extremely difficult to control the exact number of nucleotides that exonuclease removes from the 3'-end of a growing strand of nucleic acid, that level of control is not required in the methods reported herein because the feedback systems allow for the length of the strand to be determined after the error-correction steps. Therefore, if too many nucleotides are initially removed, they may be added back later.

Even though feedback and error-correction at the single-molecule level theoretically enables the synthesis of long nucleic acids, one must account for the potential that an error may occur that cannot be detected or corrected. Therefore, parallelization of single-molecule systems is desirable to ensure that the process is successful. Furthermore, parallel systems also allows for various nucleic acids of different sequences to be synthesized simultaneously. For methods and materials known in the art related to parallelization methods, see e.g., Visscher, K., Gross, S. P., Block, S. M., *Construction of Multiple-Beam Optical Traps with Nanometer-Resolution Position Sensing*, IEEE J. SELECT. TOPICS QUANT. ELECT., Vol. 2, No. 4, pages 1066-1076 (1996), which is hereby incorporated by reference.

Figure 11A:
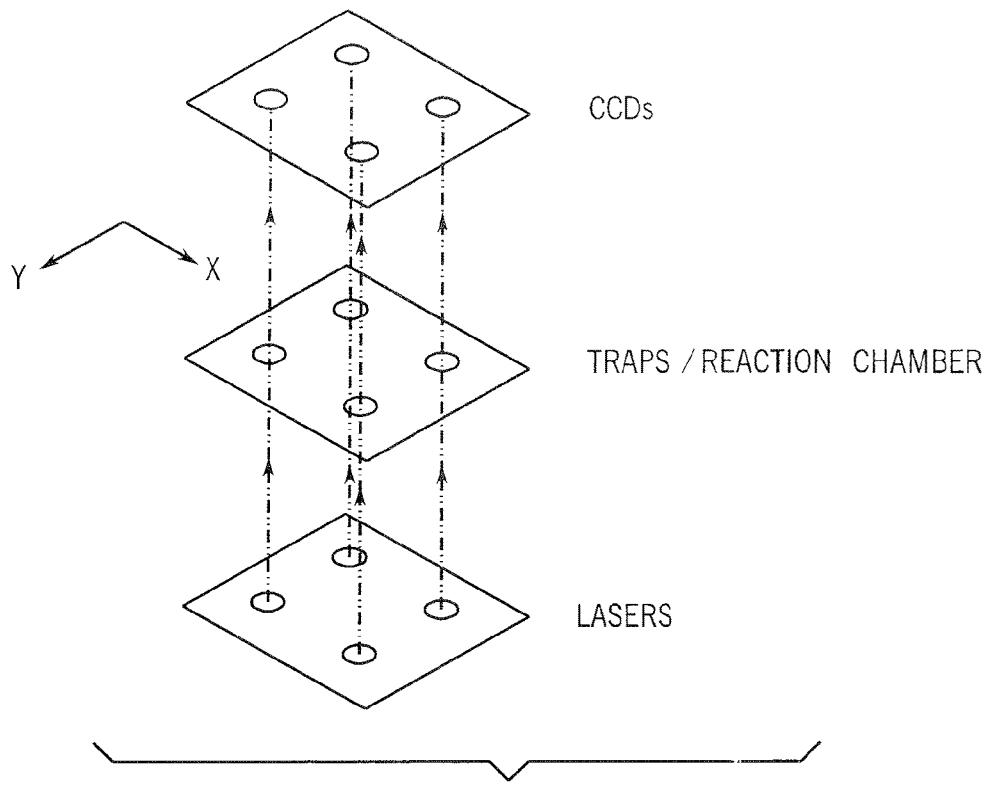
FIGS. 11A and 11B show an embodiment of the invention employing parallel single-molecule systems using single and/or multiple arrays of light sources and detectors to account for the possibility that an undetected and/or uncorrected error may have occurred and to ensure that the process is successful.

FIG. 11A. Parallel single-molecule systems using arrays of light sources and detectors. The figure shows an 8×8 array of single-molecule systems that are detected using 8×8 arrays of light sources and CCD cameras.

Figure 11B:
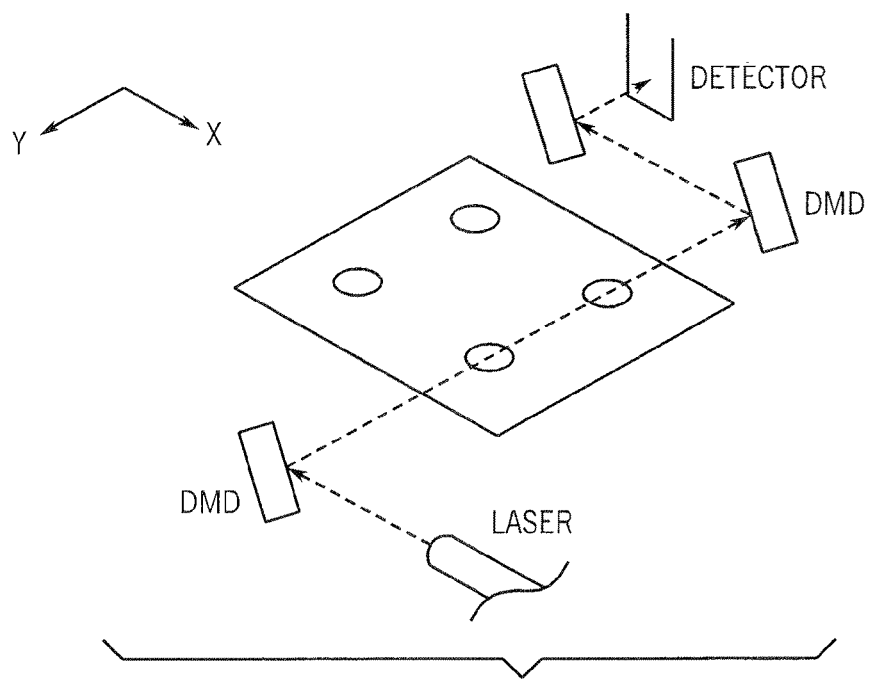

FIG. 11B. Parallel single-molecule systems using one light source and detector. The figure shows an 8×8 array of single-molecule systems, where each system is as described in FIG. 9B. Only one beam is used as the illumination source and the trapping laser, and only quadrant photodiode is used to detect all 64 systems. This is achieved by rastering the laser across all systems using a digital micromirror device (DMD). The methods shown in FIG. 11B may be combined with those in FIG. 8A, where an 8×8 array of single-molecule systems is monitored using one light source and an array of quadrant photodiodes as detectors.

This disclosure also provides for the parallelization of single-molecule systems without arrays. Single-molecule systems in which the solid-phase supports have negligible interactions can be parallelized without the use of arrays.

Figure 12A:
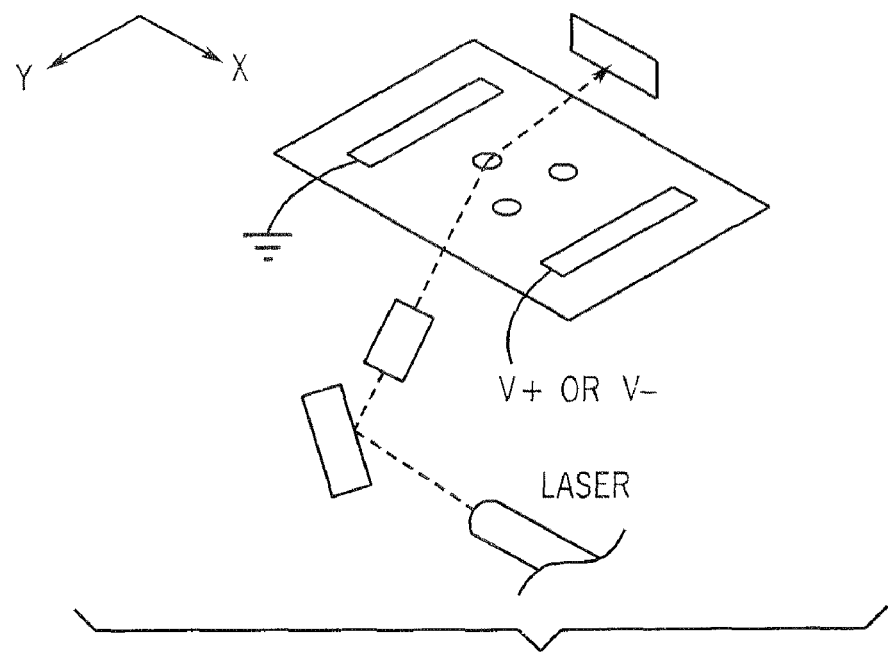
FIGS. 12A and 12B show an aspect of the invention employing parallel single-molecule systems without arrays.

FIG. 12A. In this scheme, optical tweezers are employed in the single-molecule system as described in FIG. 9B. Multiple beads in the same microscope field of view are trapped by rastering the laser beam using an acoustical-optical modulator (AOM).

Figure 12B:
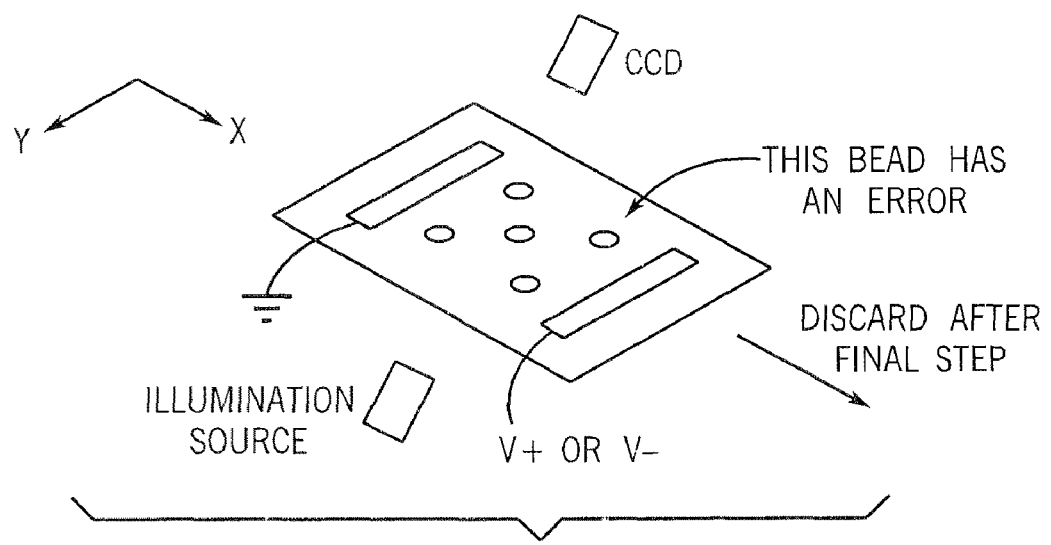

FIG. 12B. In this scheme, multiple beads are tracked using only one CCD camera. The ability to control beads independently is not available in this system. However, beads with erroneous nucleic acids can be tracked and discarded after the entire process is complete.

This disclosure also provides methods for the microfabrication of electromagnet arrays. The area density of electromagnet arrays is maximized if the electromagnets are fabricated by bulk-microfabrication techniques.

Figure 13A:
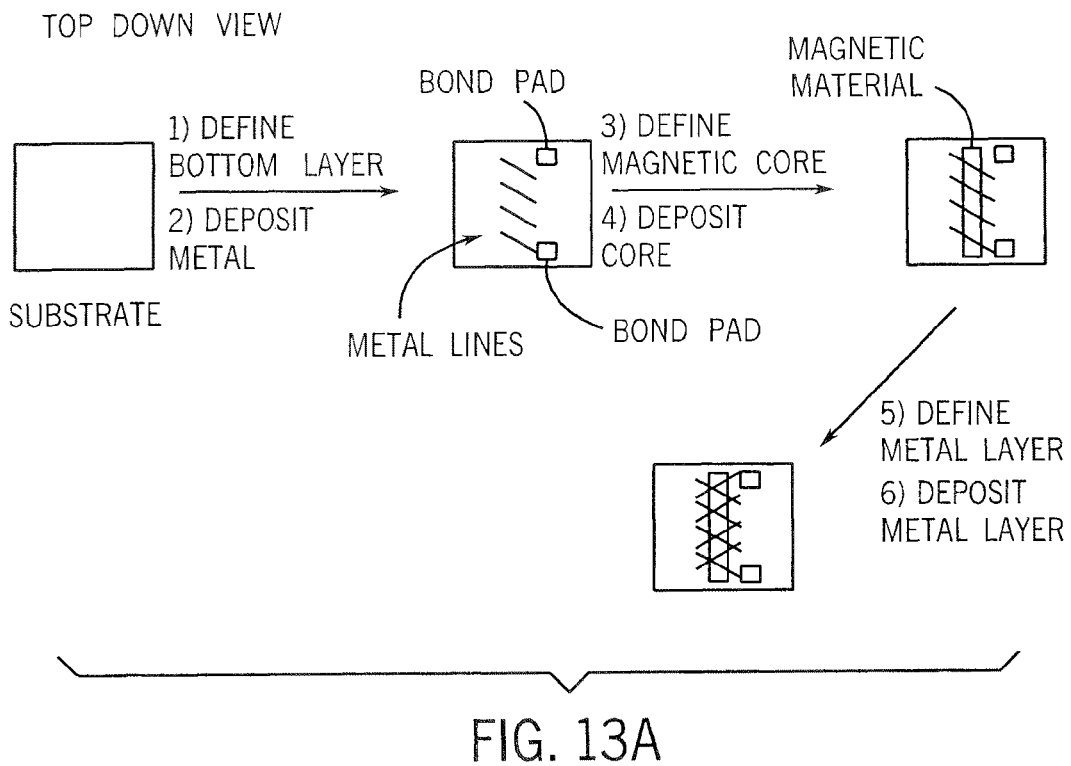
FIGS. 13A and 13B show a method for the microfabrication of quadrupole arrays.

FIG. 13A shows a scheme for the microfabrication of quadrupole arrays. First, a layer of diagonal metal wires are lithographically defined and deposited on a silicon substrate.

Bond pads are also defined in this first step. Then, a film of soft magnetic material is lithographically designed and deposited over a portion of the metal lines. A second layer of metal lines are lithographically defined and deposited over the magnetic film layer to complete the microfabrication of in-plane microelectromagnets.

Figure 13B:
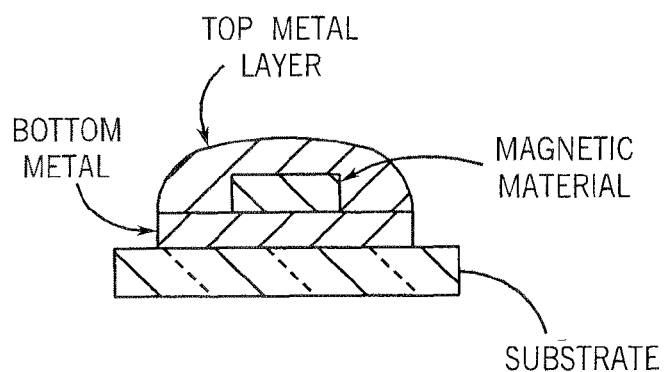

FIG. 13B shows the cross section of such a microfabricated electromagnet.

Figure 14A:
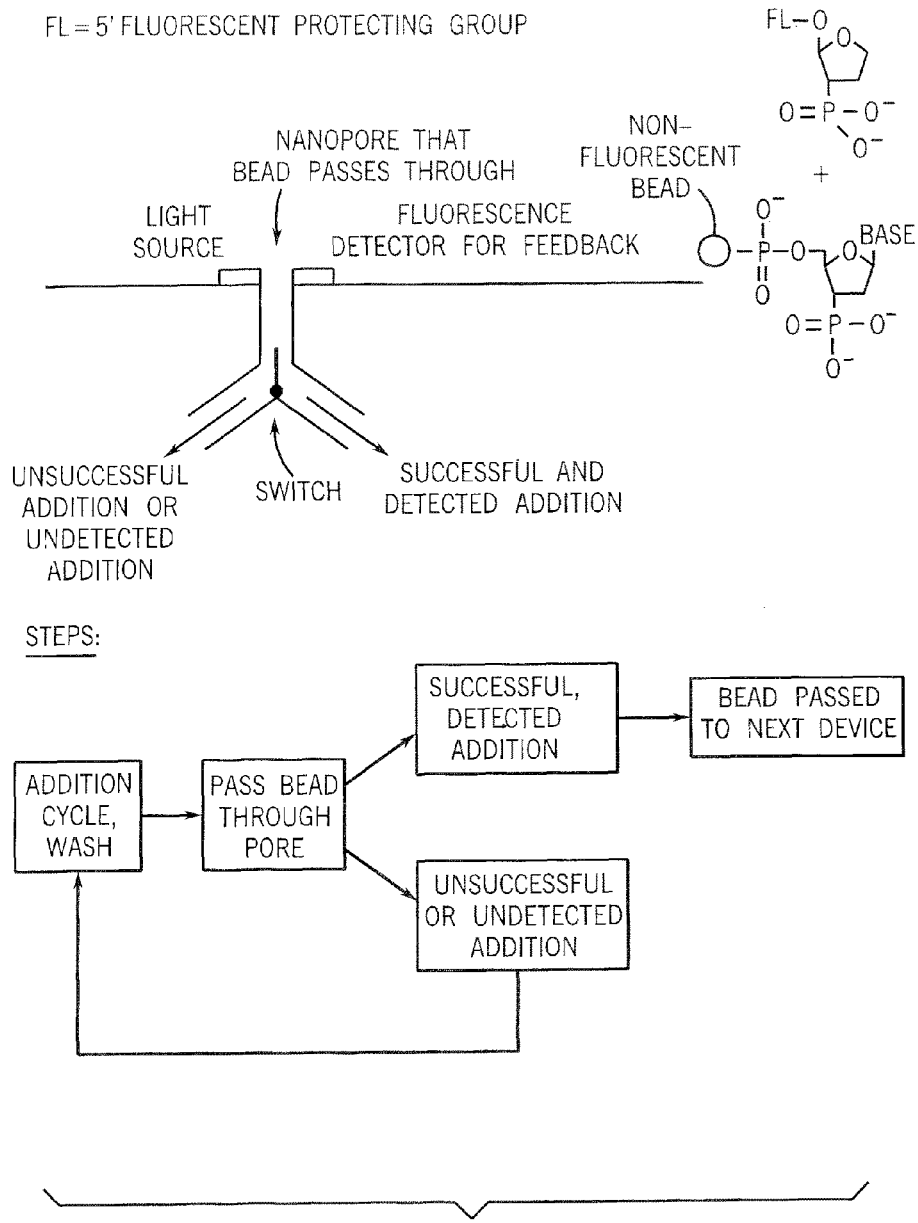
FIGS. 14A and 14B show an embodiment of the invention for error checking and error correction using nanopore devices for single-molecule synthesis with feedback using fluorescent 5' protecting groups.
Figure 14B:
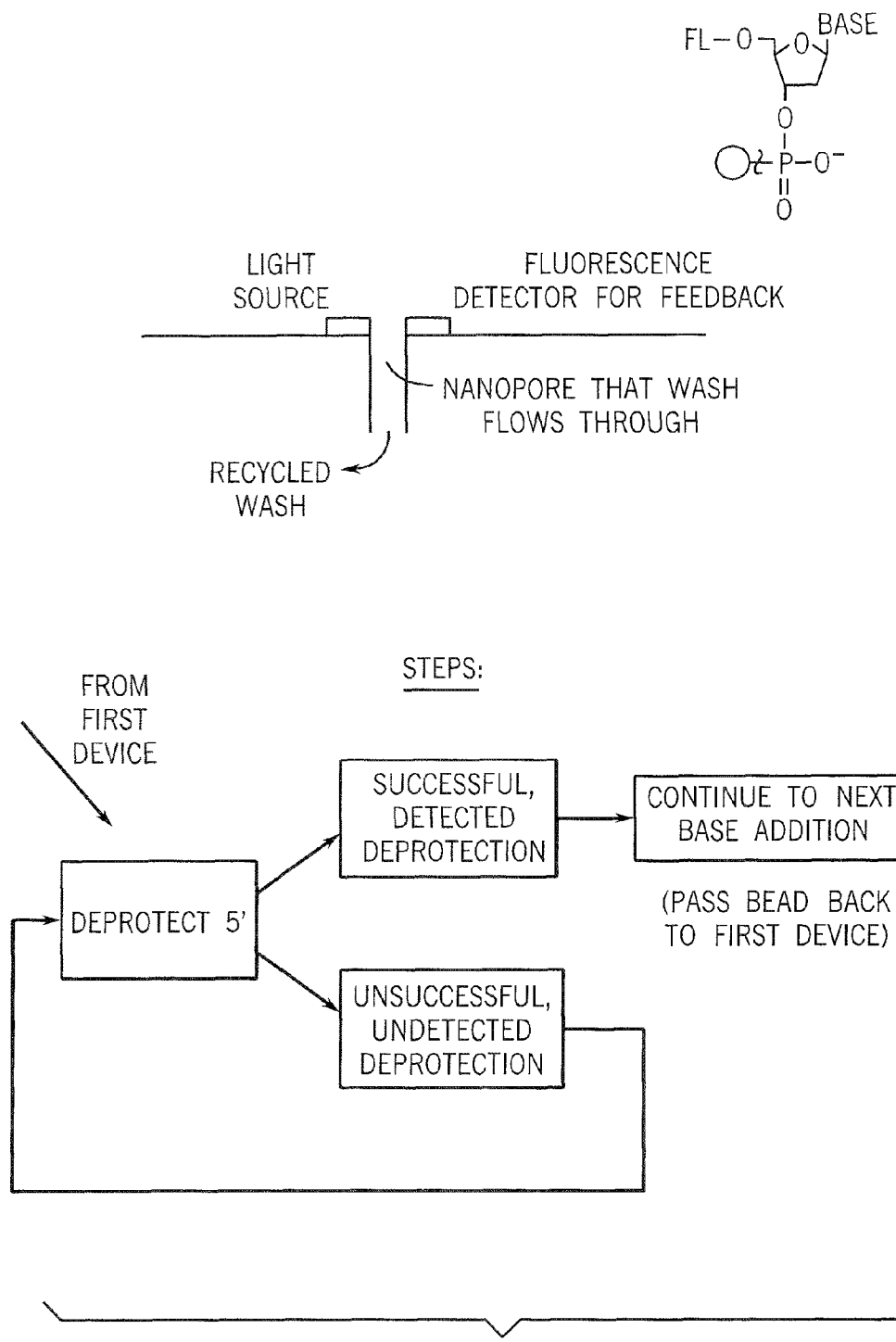

FIGS. 14A and 14B. Nanopore devices for single-molecule synthesis.

FIG. 14A shows the design of a nanopore device for single-molecule synthesis with feedback using 5' protecting groups that may be fluorescent. DNA is synthesized on a non-fluorescent solid support and passes through a channel opening, known in the art as a nanopore, with a detector. The bead can be directed to one of two channels by a switch, depending on whether a successful addition has occurred. After the coupling step and removal of excess reagents, the bead is passed through the pore. The addition can be detected by different means, such as but not limited to, capacitive measurements (across the channel corresponding to oligonucleotide length) or fluorescence. For example, fluorescence measurements can be used to detect additions if 5' fluorescent protecting groups are used. A detected increase in length corresponds to a successful addition. If no addition is detected, either the coupling reaction was unsuccessful, or it was successful but not detected. The bead is directed back into the device for another coupling step. Because the 5' end of the growing strand is protected, a redundant coupling step will not result in multiple-base addition. Once the addition is successful and detected, the bead is passed into the device described in FIG. 9B. For methods and materials known in the art related to nanopore analysis see, e.g., Deamer, D. W., Branton, D., *Characterization of Nucleic Acids by Nanopore Analysisl*, ACC. CHEM. RES., Vol. 35, No. 10, 817-825 (2002), which is hereby incorporated by reference.

FIG. 14B shows the design of a second nanopore device for single-molecule synthesis with feedback using fluorescent 5' protecting groups. Monitoring the deprotection of the 5' group is necessary to eliminate deletion errors. In this device, the growing strand is deprotected, and the wash is flowed through the nanopore, not the bead, and the nanopore only leads to one channel. If no fluorescence is detected in the wash, then the strand was not deprotected, or it was successfully deprotected but the fluorescent protecting group was not detected. The wash is constantly recycled until a fluorescent group is detected. Because there are no free nucleotides (only the growing strand) in this device, no addition error can occur by redundant 5' deprotection steps. Once the freed protecting group is detected, the bead is passed back to the device described in FIG. 9A for a subsequent base addition. Many materials are known in the art relating to nanopore analysis.

FIGS. 15A-G show an example of the independent control of a cluster of superparamagnetic beads by an electric field and opposing magnetic field gradient. These are screenshots obtained from a CCD camera mounted on a microscope. In each screenshot, the electrophoretic force moves the beads to the left of the screen, and the magnetic field gradient moves the bead to the right of the screen (i.e. the positive electrode is outside and towards the left of the field-of-view, and the magnetic tweezer apparatus is outside and towards the right of the field-of-view).

Figure 15A:
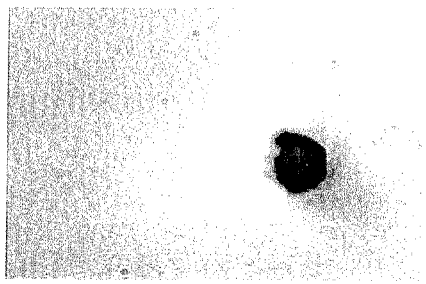
FIGS. 15A-G illustrate the independent control of a cluster of superparamagnetic beads by an electric field and opposing magnetic field gradient.

FIG. 15A. The electric field is on and the magnetic field is off. The beads are initially moving to the left because the electrophoretic force exceeds the magnetophoretic force.

Figure 15B:
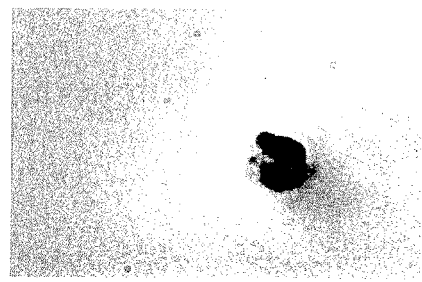

FIG. 15B. The electric field is on and the magnetic field is turned on. The motion of the beads stops because the opposing forces are equal.

Figure 15C:
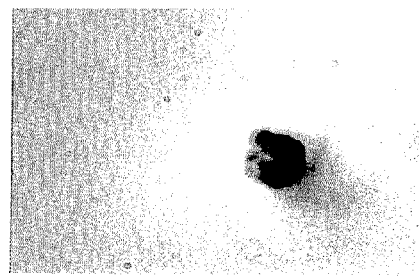

FIG. 15C. The magnetic field is increased. The beads move to the right because the magnetophoretic force exceeds the electrophoretic force.

Figure 15D:
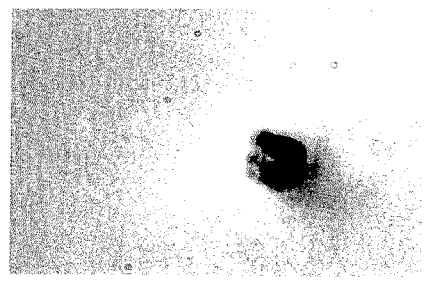

FIG. 15D. The electric field is increased. The motion of the beads stops because the opposing forces are equal.

Figure 15E:
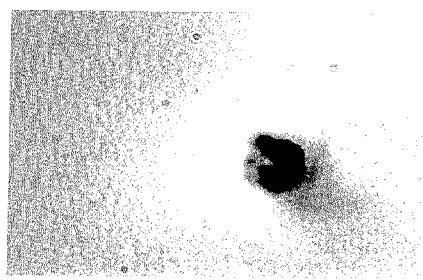

FIG. 15E. The electric field is further increased. The beads move left as the electrophoretic force exceeds the magnetophoretic force.

Figure 15F:
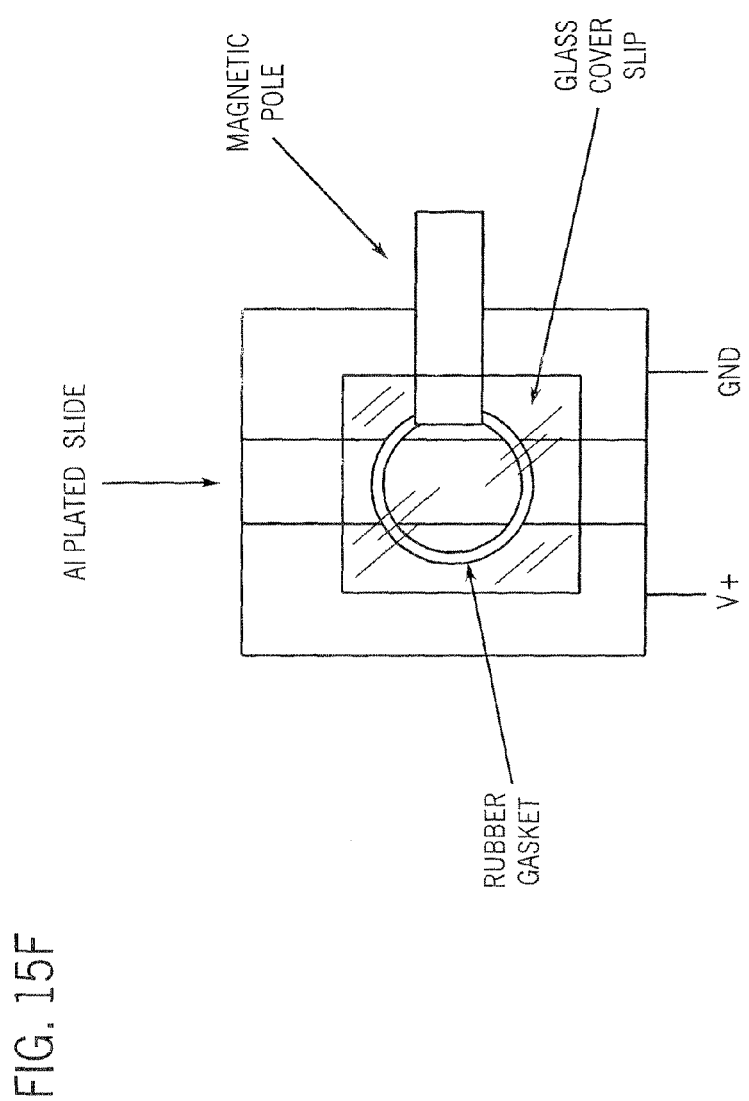
Figure 15G:
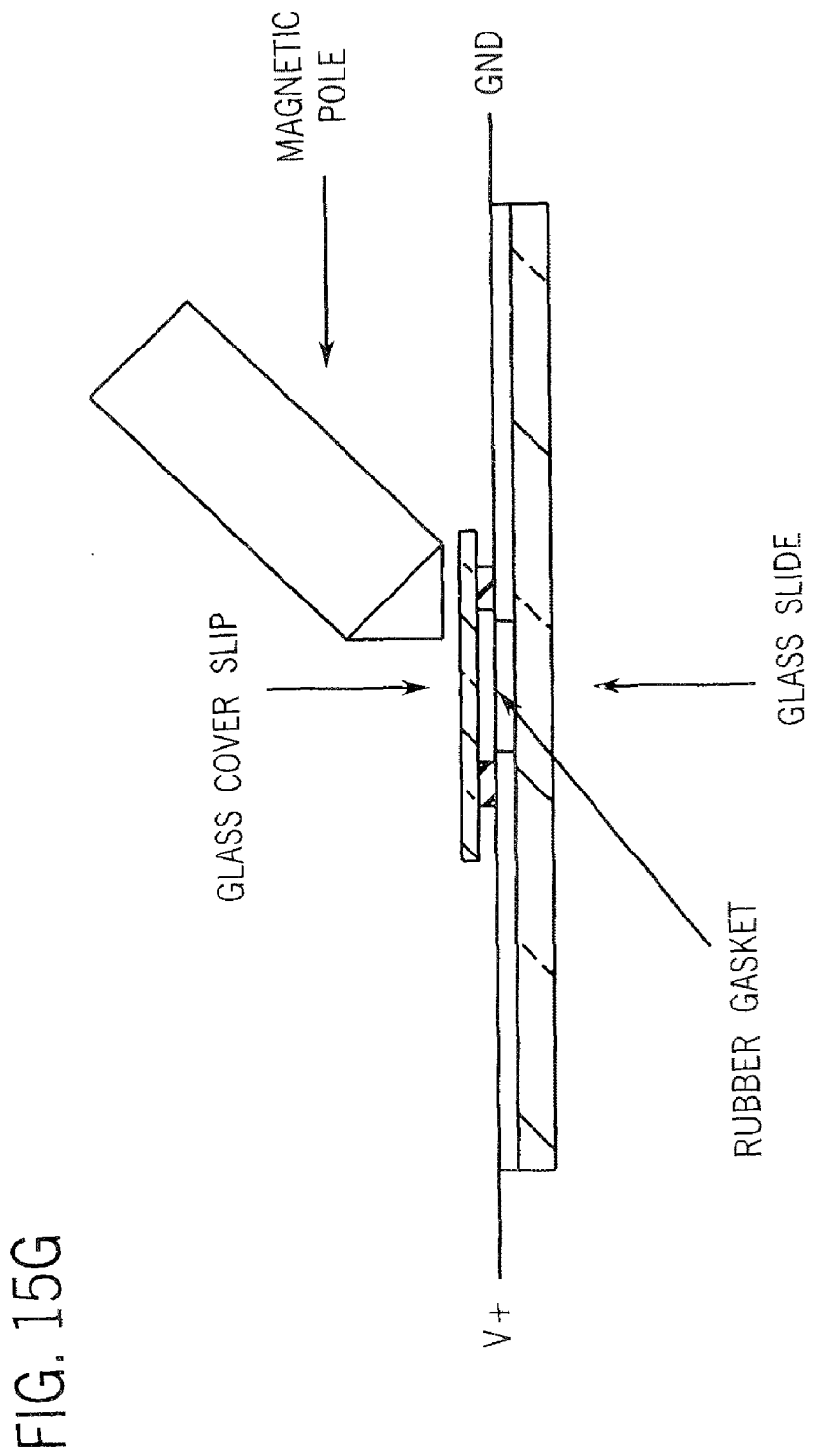

FIGS. 15F and 15G. The experimental system schematic is shown in FIGS. 15F and 15G below, and the experimental details can be found in the accompanying description of FIGS. 15F and 15G. FIGS. 15F and 15G depict a method for the construction of an electrophoretic reservoir and magnetic tweezer. Superparamagnetic beads 1.05 μm in diameter were obtained from Dynal Biotech (DynaBeads MyOne Carboxylic Acid). Beads were washed according to standard protocols and dispersed in distilled water. The electrode structure was made by thermal evaporation of aluminum on a glass slide. The electrodes were spaced apart by about 1 cm using kapton tape as a mask. The reservoir was created by first placing an o-ring between the aluminum pads, and then sealing the reservoir with a glass cover slip. The single-pole magnetic tweezer was placed approximately 3 mm from the ground electrode, such that the attractive magnetic field gradient opposed the electrophoretic force felt by the beads. The single-pole magnetic tweezer was composed of a tip-pole electromagnet with a laser-cut scaffold to bring the tip of the tweezer as close to the top coverslip as possible. The core of the electromagnet was about 25 mm in length and about 10 mm in diameter. It was wrapped about 300 times with insulated copper wire that was potted using epoxy. The tips of the electromagnets were cut at about a 45° using a diamond saw. The current through the electromagnet and voltage across the electrodes were controlled using custom written software written in Labview. The entire apparatus was placed on the stage of a custom built optical microscope with a 20× condenser lens and 100× objective lens. Images were collected using a CCD camera and frame grabber that output to the software.

A preferred embodiment of the invention is directed toward the removal of double-stranded oligonucleotides containing sequence mismatch errors. It is particularly related to the removal of error-containing oligonucleotides generated, for example, by chemical or biological synthesis by removing mismatched duplexes using mismatch recognition proteins. For methods and materials known in the art related to error detection and correction using mismatch binding proteins, see e.g., Tabone, et al., WIPO application 03/054232A2 titled *Methods for Removal of Double-Stranded Oligonucleotides Containing Sequence Errors Using Mismatch Recognition Proteins*, which is hereby incorporated by reference.

FIGS. 16A-C. Removal of error sequences using mismatch binding proteins. An error in a single strand of DNA causes a mismatch in a DNA duplex. A mismatch recognition protein (MMBP), such as a dimer of MutS, binds to this site on the DNA.

FIG. 16A. A pool of DNA duplexes contains some with mismatches (left) and some which are error-free (right). The 3'-terminus of each DNA strand is indicated by an arrowhead. An error giving rise to a mismatch is shown as a raised triangular bump on the top left strand. A MMBP is added and binds selectively to the site of the mismatch. The MMBP-bound DNA duplex is removed, leaving behind a pool which is dramatically enriched for error-free duplexes.

FIG. 16B. The DNA-bound protein provides a means to separate the error-containing DNA from the error-free copies. The protein-DNA complex can be captured by affinity of the protein for a solid support bearing such as a specific antibody, immobilized nickel ions (protein is produced as a his-tag fusion), streptavidin (protein has been modified by the covalent addition of biotin) or by any other such mechanisms as are common to the art of protein purification.

FIG. 16C. Alternatively, the protein-DNA complex is separated from the pool of error-free DNA sequences by a difference in mobility, such as by size-exclusion column chromatography or by electrophoresis. In this example, the electrophoretic mobility in a gel is altered upon MMBP binding: in the absence of MMBP all duplexes migrate together, but in the presence of MMBP, mismatch duplexes are retarded (upper band). The mismatch-free band (lower) is then excised and extracted.

Figure 17:
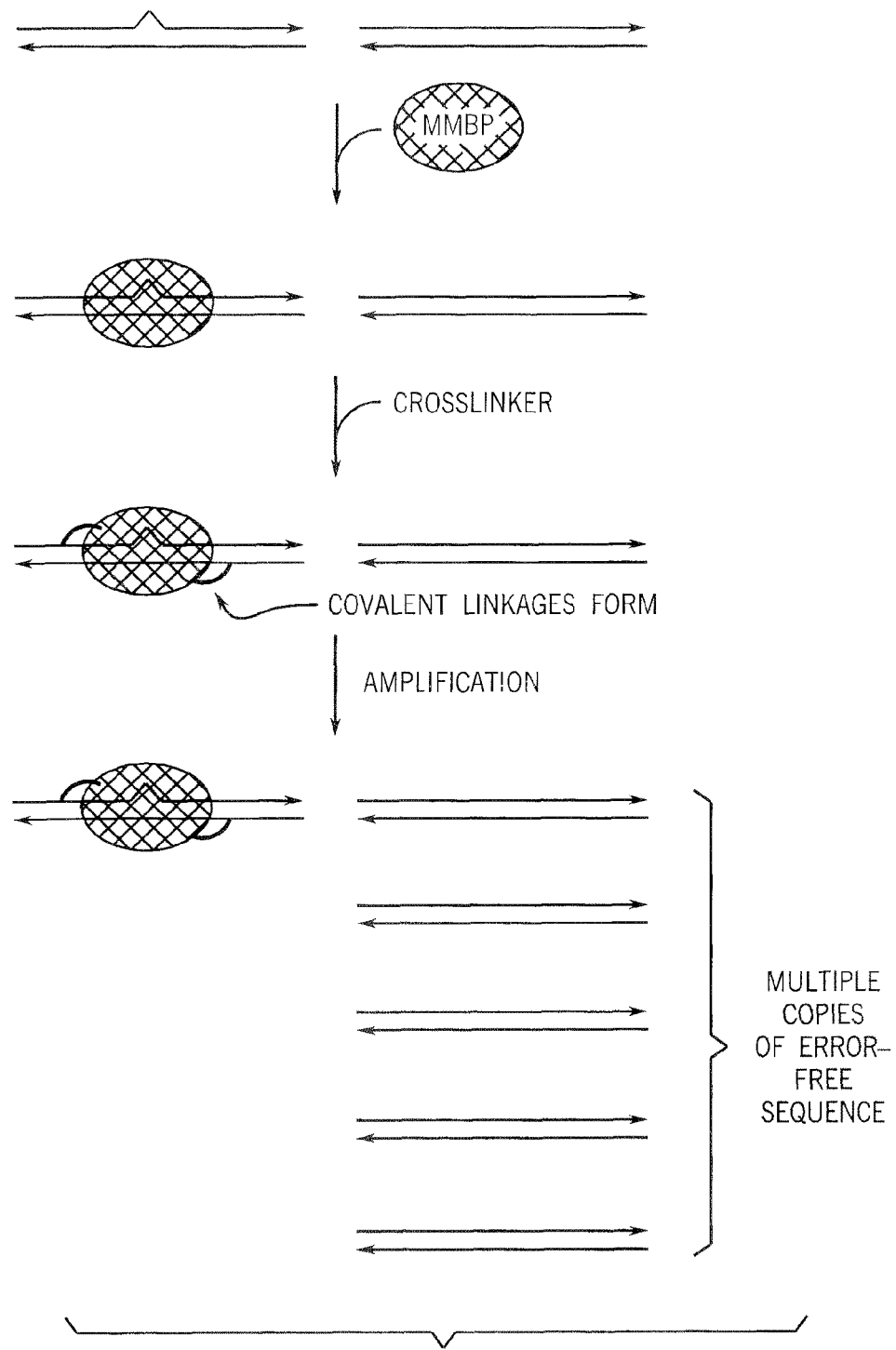
FIG. 17 shows an aspect of the invention for removing and correcting error sequences using chemical crosslinking agents complexed with MMBP. The pool of nucleotide sequences can then be amplified, and those containing errors bound with the MMBP crosslinking agent complex will be quickly outnumbered by the error free nucleotide sequences.

FIG. 17. Neutralization of error sequences with mismatch recognition proteins. The error-containing DNA sequence is not removed from the pool of DNA products. Rather, it becomes irreversibly complexed with a mismatch recognition protein by the action of a chemical crosslinking agent (for example, dimethyl suberimidate, DMS), or of another protein (such as MutL). The pool of DNA sequences is then amplified (such as by the polymerase chain reaction, PCR), but those containing errors are blocked from amplification, and quickly become outnumbered by the increasing error-free sequences. As in FIG. 6A, a pool of DNA duplexes contains some DNA duplexes with mismatches (left) and some which are error-free (right). A MMBP binds selectively to the DNA duplexes containing mismatches. Application of a crosslinking agent irreversibly attaches MMBP at the site of the mismatch. Amplification of the pool of DNA duplexes produces more copies of the error-free duplexes. The MMBP-mismatch DNA complex is unable to participate in amplification because the bound protein prevents the two strands of the duplex from dissociating. For long DNA duplexes, the regions outside the MMBP-bound site may be able to partially dissociate and participate in partial amplification of those (error-free) regions.

As increasingly longer sequences of DNA are generated, the fraction of sequences which are completely error-free diminishes. At some length, it becomes likely that there will be no molecule in the entire pool which contains a completely correct sequence. Thus, for the generation of extremely long segments of DNA, it can be useful to produce smaller units first which can be subjected to the above error control approaches. Then these segments can be combined to yield the larger full length product. However, if errors in these extremely long sequences can be corrected locally, without removing or neutralizing the entire long DNA duplex, then the more complex stepwise assembly process can be avoided.

Many biological DNA repair mechanisms rely on recognizing the site of a mutation (error) and then using a template strand (most likely error-free) to replace the incorrect sequence. In the de novo production of DNA sequences, this process is complicated by the difficulty of determining which strand contains the error and which should be used as the template. In this invention, the solutions to this problem rely on using the pool of other sequences in the mixture to provide the template for correction. These methods can be very robust: even if every strand of DNA contains one or more errors, as long as the majority of strands have the correct sequence at each position (expected because the positions of errors are generally not correlated between strands), there is a high likelihood that a given error will be replaced with the correct sequence. FIGS. 18, 19, 20A-B, 21A-B, 22, 23A-B, and 24 present procedures for performing this sort of local error correction.

Strand-specific error correction. In replicating organisms, enzyme-mediated DNA methylation is often used to identify the template (parent) DNA strand. The newly synthesized (daughter) strand is at first unmethylated. When a mismatch is detected, the hemimethylated state of the duplex DNA is used to direct the mismatch repair system to make a correction to the daughter strand only. However, in the de novo synthesis of a pair of complementary DNA strands, both strands are unmethylated, and the repair system has no intrinsic basis for choosing which strand to correct. In this aspect of the invention, methylation and site-specific demethylation are employed to produce DNA strands that are selectively hemimethylated. A methylase, such as the Dam methylase of *E. coli*, is used to uniformly methylate all potential target sites on each strand. The DNA strands are then dissociated, and allowed to re-anneal with new partner strands. A new protein is applied, a fusion of a mismatch binding protein (MMBP) with a demethylase. This fusion protein binds only to the mismatch, and the proximity of the demethylase removes methyl groups from either strand, but only near the site of the mismatch. A subsequent cycle of dissociation and annealing allows the (demethylated) error-containing strand to associate with a (methylated) strand which is error-free in this region of its sequence. (This should be true for the majority of the strands, since the locations of errors on complementary strands are not correlated.) The hemi-methylated DNA duplex now contains all the information needed to direct the repair of the error, employing the components of a DNA mismatch repair system, such as that of *E. coli*, which employs MutS, MutL, MutH, and DNA polymerase proteins for this purpose. The process can be repeated multiple times to ensure all errors are corrected.

Figure 18:
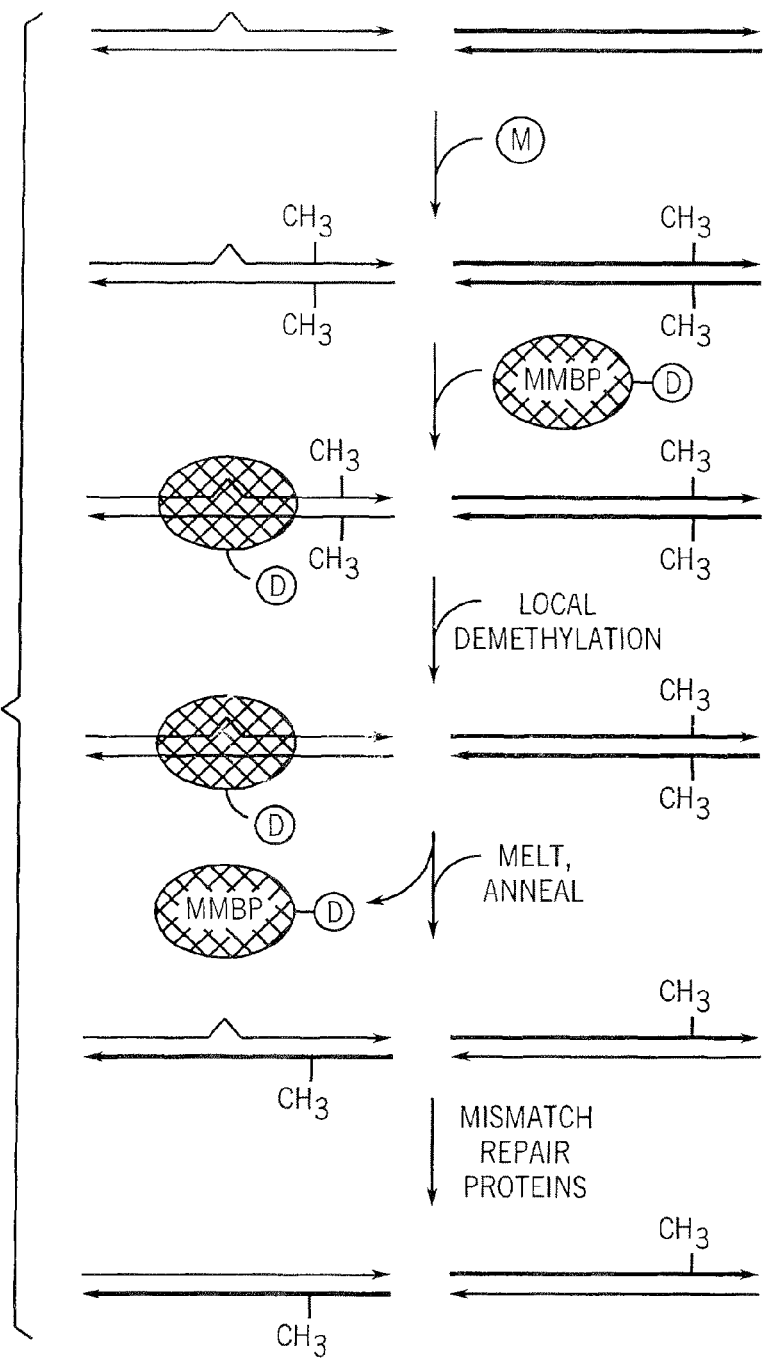
FIG. 18 shows an aspect of the invention for strand-specific error correction utilizing methylation and site-specific demethylation.

FIG. 18. Two DNA duplexes are shown, identical except for a single base error in the top left strand, giving rise to a mismatch. The strands of the right hand duplex are shown with thicker lines. Action of a methylase(M) uniformly methylates all possible sites on each DNA strand. The methylase is removed, and a protein fusion is applied, containing both a mismatch binding protein (MMBP) and a demethylase (D). The MMBP portion of the fusion protein binds to the site of the mismatch. Action of the demethylase portion of the fusion protein removes methyl groups from both strands in the vicinity of the mismatch. The MMBP-D protein fusion is removed, and the DNA duplexes are allowed to dissociate and re-associate with new partner strands. The error-containing strand will most likely re-associate with a complementary strand which a) does not contain a complementary error at that site; and b) is methylated near the site of the mismatch. This new duplex now mimics the natural substrate for DNA mismatch repair systems. Application of the components of a mismatch repair system (such as *E. coli* MutS, MutL, MutH, and DNA polymerase) removes bases in the error-containing strand (including the error), and uses the opposing (error-free) strand as a template for synthesizing the replacement, leaving a corrected strand.

Figure 19:
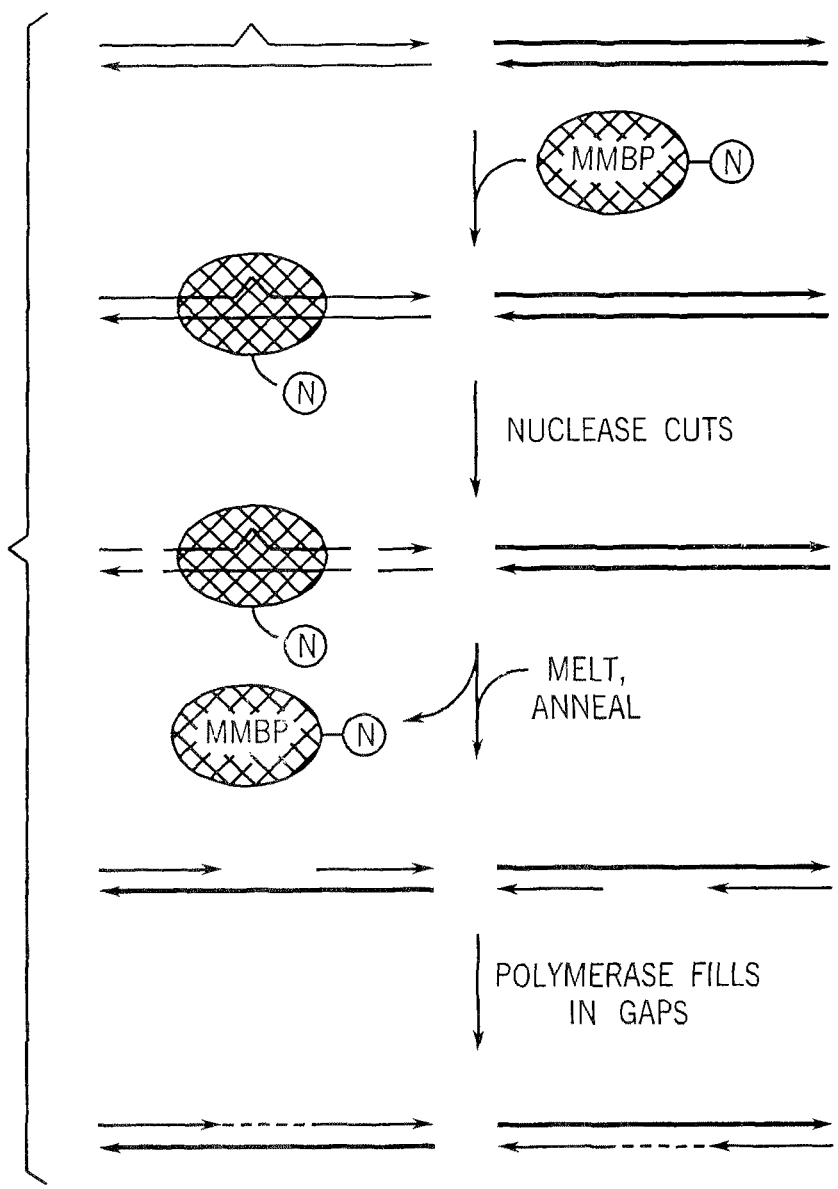
FIG. 19 shows an aspect of the invention for removing and correcting error sequences using a MMBP fusion to a non-specific nuclease.
Figure 20A:
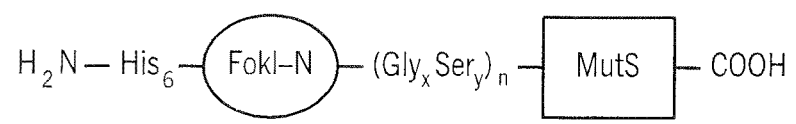
FIGS. 20A and 20B show an aspect of the invention for removing and correcting error sequences using a MMBP fusion to a non-specific nuclease. The MMBP binds to a mismatch in a DNA duplex; the MMBP-bound DNA complex is then removed using methods of protein purification.
Figure 20B:
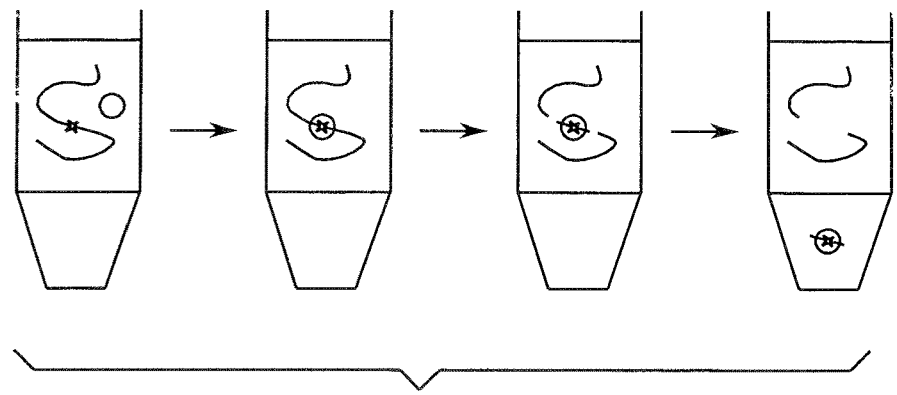

In a preferred embodiment of the invention, errors are detectable in the form of a DNA mismatch, and can be removed by the combined action of 1) a protein, molecule, or process which recognizes mismatches; and 2) a second protein, molecule, or process which cleaves the DNA. FIG. 19 illustrates a process for removing errors utilizing a mismatch recognition function in cooperation with a DNA cleavage agent. FIGS. 20A and 20B demonstrate one possible design for an agent capable of combining these two functions.

Local removal of DNA on both strands at the site of a mismatch is possible. Various means can be used to create a break in both DNA strands near an error. For example, a MMBP fusion to a non-specific nuclease (such as DNAseI) can direct the action of the nuclease (N) to the mismatch site, cleaving both strands. Once the break is generated, homologous recombination can be employed to use other strands (most of which will be error-free at this site) as template to replace the excised DNA. For example, the RecA protein can be used to facilitate single strand invasion, an early step in homologous recombination. Alternatively, a polymerase can be employed to allow broken strands to reassociate with new full-length partner strands, synthesizing new DNA to replace the error.

FIG. 19. Two DNA duplexes are shown, identical except that one contains a single base error as in FIG. 18. A protein, such as a fusion of a MMBP with a nuclease (N), binds at the site of the mismatch. Alternatively, a nuclease with specificity for single-stranded DNA can be employed, using elevated temperatures to favor local melting of the DNA duplex at the site of the mismatch. (In the absence of a mismatch, a perfect DNA duplex will be less likely to melt.) Action of an endonuclease, such as that of the MMBP-N fusion, makes double-stranded breaks near the site of the mismatch. The MMBP-N complex is removed, along with the bound short region of DNA duplex around the mismatch. Melting and re-annealing of partner strands produces some duplexes with single-stranded gaps. A DNA polymerase is used to fill in the gaps, producing DNA duplexes without the original error.

FIGS. 20A and 20B. A protein designed to combine the functions of error recognition and error removal. The gene for a mismatch recognition protein (such as MutS) has been linked to the gene for a nuclease domain (such as that of restriction endonuclease FokI). When this gene is expressed, both functions will be combined in the same protein molecule, which will contain two separately folded domains. As MutS forms a dimer, so will this designed protein, allowing it to bind DNA at the site of a mismatch and cut both strands of DNA, excising the segment which contains an error, as shown in FIG. 19. In a preferred embodiment of the invention, the designed protein would be thermostable. For example the binding and nuclease domains could be derived from thermophilic organisms, or proteins could be engineered for thermostability. This feature would allow the protein to function in a thermally cycled reaction, such as PCR or LCR, allowing error correction to occur in tandem with assembly of molecules of nucleic acid.

FIG. 20A. A designed protein for error recognition and removal. The *E. coli* mismatch recognition protein MutS and restriction endonuclease FokI nuclease domain are used here as an example. These proteins can be produced as a part of a single polypeptide chain. A linker between the domains provides the flexibility for both domains to contact the same molecule(s) of nucleic acid. Additional amino acid sequences can be added to the design, such as an affinity tag (a Histidine tag is shown here) used in purification.

FIG. 20B. A single tube process for assembling or amplifying molecules of nucleic acid while correcting errors. A tube or chamber for thermocycled reactions is divided into two regions, separated by a membrane. As the nucleic acids are assembled (or amplified), a thermostable protein (as in FIG. 20A) acts on the nucleic acid to remove errors. The small pieces of excised error-containing DNA are the only ones small enough to pass through the membrane to the other side of the chamber. Here they encounter a resin with affinity for nucleic acid, so that they are not able to pass back into the other chamber, and are effectively removed from the desired nucleic acid product. Reassembly of the nucleic acid molecules surviving this process can be accomplished in many ways (see FIGS. 19, 21A-B, 22, and 23A-B), including a PCR reaction that can take place in the same reaction. Multiple thermal cycles dissociate and reassociate the DNA duplexes. Where errors may still be present, this reassortment of individual strands provides new templates for error correction.

Figure 21A:
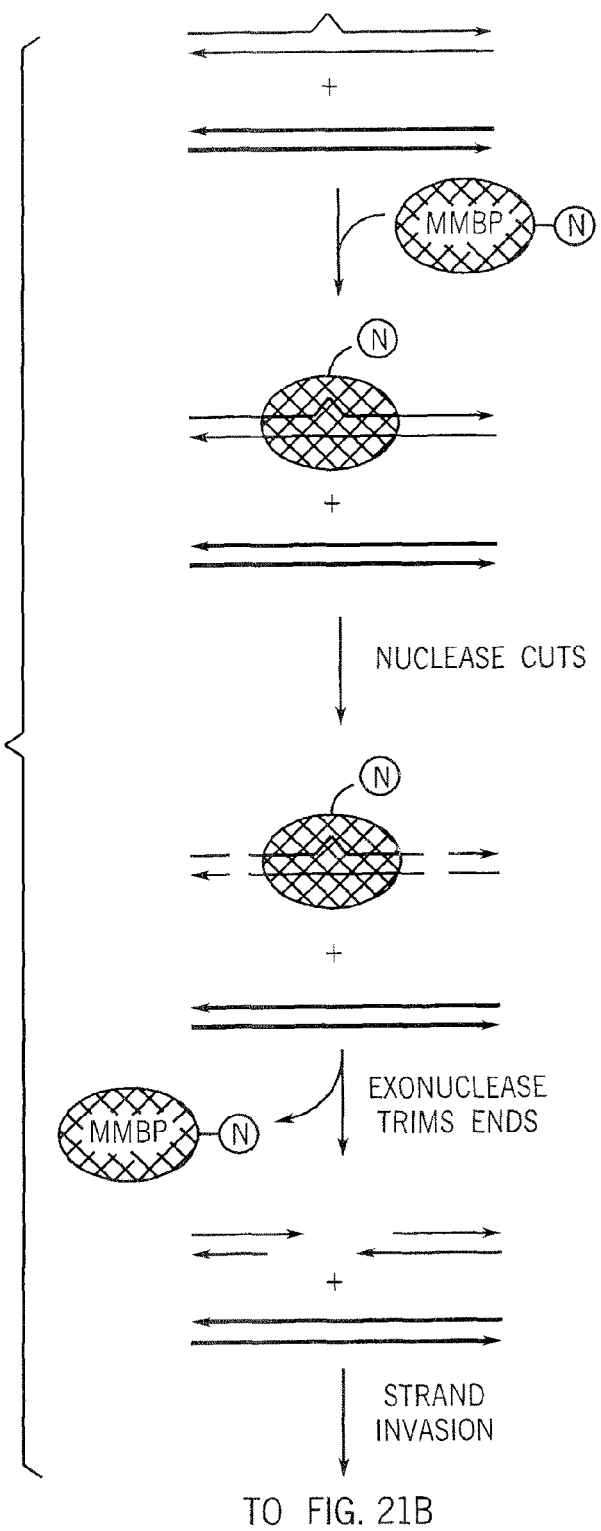

FIGS. 21A and 21B follow a process similar to that of FIG. 19. However, in this embodiment of the invention, double-stranded gaps in DNA duplexes are repaired using the protein components of a recombination repair pathway. (Note that in this case global melting and re-annealing of DNA strands is not an absolute requirement, which can be preferable when dealing with especially large DNA molecules, such as genome length DNA.)

FIG. 21A. Two DNA duplexes are shown, identical except that one contains a single base mismatch. A protein, such as a fusion of a MMBP with a nuclease (N), is added to bind at the site of the mismatch. Action of an endonuclease, such as that of the MMBP-N fusion, makes double-stranded breaks around the site of the mismatch. Protein components of a DNA repair pathway, such as the RecBCD complex, are employed to further digest the exposed ends of the double-stranded break, leaving 3' overlaps.

FIG. 21B. Protein components of a DNA repair pathway, such as the RecA protein, are employed to facilitate single strand invasion of the intact DNA duplex, forming a Holliday junction. A DNA polymerase synthesizes new DNA, filling in the single-stranded gaps. Protein components of a DNA repair pathway are employed, such as the RuvC protein, to resolve the Holliday junction(s). The two resulting DNA duplexes do not contain the original error. Note that there can be more than one way to resolve such junctions, depending on migration of the branch points.

Figure 22:
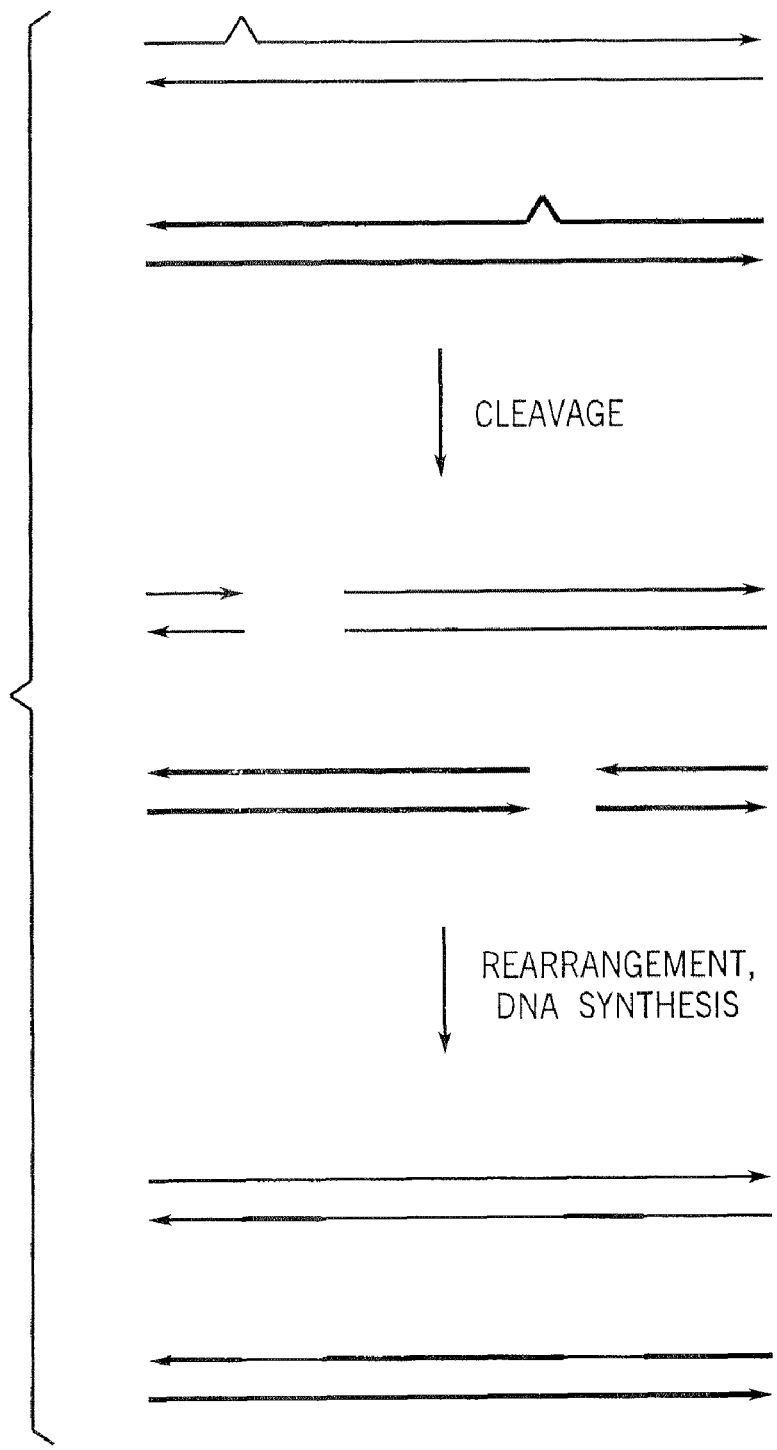
FIG. 22 shows an aspect of the invention for removing and correcting error sequences using a MMBP fusion to a non-specific nuclease.

It is important to make clear that the methods of this invention are capable of generating large error-free DNA sequences, even if none of the initial DNA products are error-free. FIG. 22 summarizes the effects of the methods of FIG. 19 (or equivalently, FIGS. 21A-B) applied to two DNA duplexes, each containing a single base (mismatch) error.

FIG. 22. Two DNA duplexes are shown, identical except for a single base mismatch in each, at different locations in the DNA sequence. Mismatch binding and localized nuclease activity are used to generated double-stranded breaks which excise the errors. Recombination repair (as in FIGS. 21A-B) or melting and reassembly (as in FIG. 19) are employed to generate DNA duplexes where each excised error sequence has been replaced with newly synthesized sequence, each using the other DNA duplex as template (and unlikely to have an error in that same location). Note that complete dissociation and re-annealing of the DNA duplexes is not necessary to generate the error-free products (if the methods shown in FIGS. 21A-B are employed)

A simple way to reduce errors in long DNA molecules is to cleave both strands of the DNA backbone at multiple sites, such as with a site-specific endonuclease which generates short single stranded overhangs at the cleavage site. Of the resulting segments, some are expected to contain mismatches. These can be removed by the action and subsequent removal of a mismatch binding protein, as described in FIG. 19. The remaining pool of segments can be re-ligated into full length sequences. As with the approach of FIGS. 21A-B, this approach includes several advantages. 1) loss of an entire full length DNA duplex is not required to remove an error; 2) global dissociation and re-annealing of DNA duplexes is not necessary; 3) error-free DNA molecules can be constructed from a starting pool in which no one member is an error-free DNA molecule.

If the most common types of restriction endonucleases were employed for this approach, all DNA cleavage sites would result in identical overhangs. Thus the segments would associate and ligate in random order. However, use of a site-specific "outside cutter" endonuclease (such as HgaI, FokI, or BspMI) produces cleavage sites adjacent to (non-overlapping) the DNA recognition site. Thus each overhang would have sequence specific to that part of the DNA, distinct from that of the other sites. The re-association of these specifically complementary cohesive ends will then cause the segments to come together in the proper order. The cohesive ends generated can be up to five bases in length, allowing for up to $4^5=1024$ different combinations. Conceivably this many distinct restriction sites could be employed, though the need to avoid near matches between cohesive ends could lower this number.

The necessary restriction sites can be specifically included in the design of the sequence, or the random distribution of these sites within a desired sequence can be utilized (the recognition sequence of each endonuclease allows prediction of the typical distribution of fragments produced). Also, the target sequence can be analyzed for which choice of endonuclease produces the most ideal set of fragments.

FIGS. 23A and 23B illustrate the semi-selective removal of mismatch-containing segments.

FIG. 23A. Three DNA duplexes, each containing one error leading to a mismatch. DNA is cut with a site-specific endonuclease, leaving double-stranded fragments with cohesive ends complementary to the adjacent segment. A MMBP is applied, which binds to each fragment containing a mismatch.

FIG. 23B. Fragments bound to MMBP are removed from the pool, as described in FIGS. 6A and 6B. The cohesive ends of each fragment allow each DNA duplex to associate with the correct sequence-specific neighbor fragment. A ligase (such T4 DNA ligase) is employed to join the cohesive ends, producing full-length DNA sequences. These DNA sequences can be error-free in spite of the fact that none of the original DNA duplexes was error-free. Incomplete ligation may leave some sequences that are less than full-length, which can be purified away on the basis of size.

According to the invention, the above approaches provide a major advantage over one of the conventional methods of removing errors, which employs sequencing first to find an error, and then relies on choosing specific error-free subsequences to "cut and paste" with endonuclease and ligase. In this embodiment of the invention, no sequencing or user choice is required in order to remove errors.

When complementary DNA strands are synthesized and allowed to anneal, both strands may contain errors, but the chance of errors occurring at the same base position in both sequences is extremely small, as discussed above. The above methods are useful for eliminating the majority case of uncorrelated errors which can be detected as DNA mismatches. In the rare case of complementary errors at identical positions on both strands (undetectable by the mismatch binding proteins), a subsequent cycle of duplex dissocation and random re-annealing with a different complementary strand (with a different distribution of error positions) remedies the problem. But in some applications it is desirable to not melt and re-anneal the DNA duplexes, such as in the case of genomic-length DNA strands. This aspect of the invention reduces correlated errors in such cases. Though the initial population of correlated errors is expected to be low, amplification or other replication of the DNA sequences in a pool will ensure that each error is copied to produce a perfectly complementary strand which contains the complementary error. According to the invention that this approach does not require global dissociation and re-annealing of the DNA strands. Essentially, various forms of DNA damage and recombination are employed to allow single-stranded portions of the long DNA duplex to re-assort into different duplexes.

Figure 24:
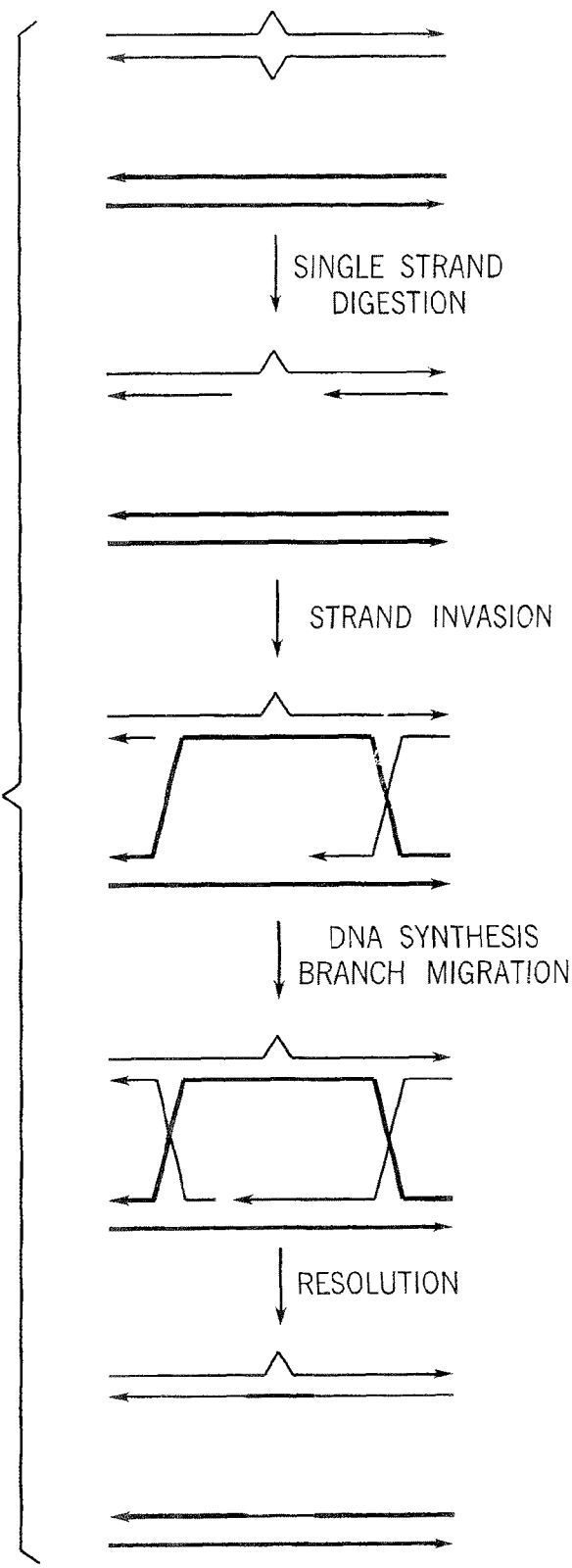
FIG. 24 shows an aspect of the invention for removing and correcting errors using recombination to generate templates for mismatch recognition of errors.

FIG. 24 shows a procedure for reducing correlated errors in synthesized DNA. Two DNA duplexes are shown, identical except for a single error in one strand. Non-specific nucleases are used to generate short single-stranded gaps in random locations in the DNA duplexes in the pool. Shown here is the result of one of these gaps generated at the site of one of the correlated locations. Recombination-specific proteins such as RecA and/or RuvB are employed to mediate the formation of a four-stranded Holliday junction. DNA polymerase is employed to fill in the gap shown in the lower portion of the complex. Action of other recombination and/or repair proteins such as RuvC is employed to cleave the Holliday junction, resulting in two new DNA duplexes, containing some sequences which are hybrids of their progenitors. In the example shown, one of the error-containing regions has been eliminated. However, since the cutting, rearrangement, and replacement of strands employed in this method is intended to be random, it is expected that the total number of errors in the sequence will actually not change, simply that errors will be reassorted to different strands. Thus, pairs of errors correlated in one duplex will be reshuffled into separate duplexes, each with a single error. This random reassortment of strands will yield new duplexes containing mismatches which can be repaired using the mismatch repair proteins detailed above. Unique to this embodiment of the invention is the use of recombination to separate the correlated errors into different DNA duplexes.

Figure 25:
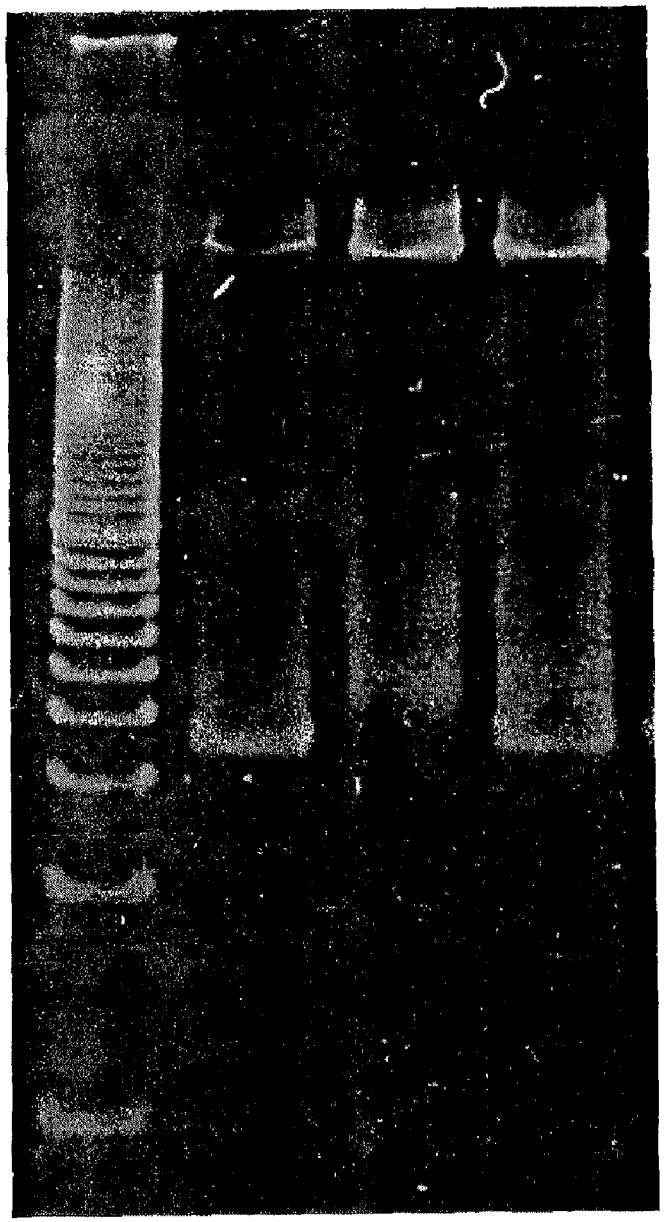
FIG. 25 shows the results of the application of MutS to removal of errors in DNA.

As an example application of mismatch repair proteins to DNA error control, MutS protein (from *T. thermophilus*, Epicentre) was used to separate an equal (50/50) mixture of double stranded DNA molecules containing both "ideal" homoduplex DNA, and an "error" duplex (mismatched heteroduplex DNA with a single base deletion in one of the strands). This experiment is shown in FIG. 25. DNA duplexes bound to MutS migrate at a slower rate (upper bands). Even the "ideal" duplexes are bound somewhat by MutS, as expected since the unpurifed oligonucleotides used for this experiment should also contain some fraction of errors. The indicated band was purified from the gel shown, and cloned into the plasmid pCR4blunt-TOPO (Invitrogen). Several of these clones (10) were also sequenced. No errors were detected in these error-filtered samples (band indicated by a white box in FIG. 25). Unfiltered samples of these duplexes were also cloned and the results sequenced. Among these samples, errors were found to be common, both the designed insertion and other random errors, at an overall frequency of 0.57 errors per clone. (The designed insertion was present in approximately 25% of the DNA stands in the 50/50 mixture.)

FIG. 25. Experimental application of MutS to removal of errors in DNA. Lower arrow: unbound duplexes. Upper arrow: duplexes bound to MutS. Lane1: 20 bp ladder (size standard). Lane 2. 69-mer double stranded DNA (no designed mismatches) and MutS protein. Most of the DNA is in the lower (unbound) fraction. Lane 3: 69-mer double stranded DNA (containing a single base insertion mismatch) and MutS. The unbound 69 bp band is absent, though a smear is visible above. Lane 4. A 50/50 mixture of the contents of lanes 2 and 3. Box: this band was excised, purified, and cloned.

The invention may be embodied in other specific forms without departing from the spirit or essential characteristics thereof. The foregoing embodiments are therefore to be considered in all respects illustrative rather than limiting on the invention described herein.

What is claimed is:

1. A method for determining whether a nucleotide or an oligonucleotide is added to a nucleic acid, the method comprising:
   a) providing a solid support having an immobilized nucleic acid, wherein the solid support is a bead or particle;
   b) performing a nucleic acid addition reaction to elongate the immobilized nucleic acid by adding a nucleotide or an oligonucleotide to the immobilized nucleic acid;
   c) after the nucleic acid addition reaction, determining whether the nucleotide or the oligonucleotide is added to the immobilized nucleic acid by detecting whether there is an increase in electrophoretic force applied to the solid support when an electric field and a magnetic field gradient are applied to the solid support, wherein the increase in electrophoretic force applied to the solid support is caused by adding the nucleotide or the oligonucleotide to the immobilized nucleic acid; and
   d) repeating steps b) and c) if the nucleotide or the oligonucleotide is not added to the immobilized nucleic acid.

2. The method of claim 1, further comprising a step of synthesizing a new immobilized nucleic acid having a desired sequence and length by repeating steps b) through d).

3. A method for synthesizing a nucleic acid having a desired sequence and length, the method comprising:
   a) providing a solid support having an immobilized nucleic acid, wherein the solid support is a bead or particle;
   b) performing a nucleic acid addition reaction to elongate the immobilized nucleic acid by adding a nucleotide or an oligonucleotide to the immobilized nucleic acid;
   c) after the nucleic acid addition reaction, determining whether the nucleotide or the oligonucleotide is added to the immobilized nucleic acid by detecting whether there is an increase in electrophoretic force applied to the solid support when an electric field and a magnetic field gradient are applied to the solid support, wherein the increase in electrophoretic force applied to the solid support is caused by adding the nucleotide or the oligonucleotide to the immobilized nucleic acid;
   d) repeating steps b) and c) if the nucleotide or the oligonucleotide is not added to the immobilized nucleic acid; and
   e) synthesizing the nucleic acid having a desired sequence and length by repeating steps b) through d).

* * * * *